(12) United States Patent
Röhl et al.

(10) Patent No.: US 10,400,269 B2
(45) Date of Patent: Sep. 3, 2019

(54) SIMULTANEOUS DETECTION OF OLIGONUCLEOTIDES, A KIT AND A USE RELATED THERETO

(71) Applicant: AXOLABS GMBH, Kulmbach (DE)

(72) Inventors: Ingo Röhl, Memmelsdorf (DE); Nadine Dörfler, Kulmbach (DE); Julia Knis, Stockheim (DE)

(73) Assignee: AXOLABS GMBH, Kumlbach (DE)

( * ) Notice: Subject to any disclaimer, the term of this patent is extended or adjusted under 35 U.S.C. 154(b) by 0 days.

(21) Appl. No.: 15/554,456

(22) PCT Filed: Mar. 2, 2016

(86) PCT No.: PCT/EP2016/054450
§ 371 (c)(1),
(2) Date: Aug. 30, 2017

(87) PCT Pub. No.: WO2016/139262
PCT Pub. Date: Sep. 9, 2016

(65) Prior Publication Data
US 2018/0073060 A1 Mar. 15, 2018

(30) Foreign Application Priority Data
Mar. 2, 2015 (EP) .................................. 15000588

(51) Int. Cl.
*C12Q 1/6816* (2018.01)
(52) U.S. Cl.
CPC .................... *C12Q 1/6816* (2013.01)
(58) Field of Classification Search
None
See application file for complete search history.

(56) References Cited

U.S. PATENT DOCUMENTS

2003/0064524 A1 4/2003 Gjerde et al.

FOREIGN PATENT DOCUMENTS

| WO | 2010/043512 | 4/2010 |
| WO | 2012/109157 | 8/2012 |

OTHER PUBLICATIONS

Bartel, David P. et al., "MicroRNAs: Target Recognition and Regulatory Functions", Cell, Jan. 23, 2009, vol. 136, Issue 2, pp. 215-233.

(Continued)

*Primary Examiner* — Joseph G. Dauner
(74) *Attorney, Agent, or Firm* — Medler Ferro Woodhouse & Mills PLLC

(57) ABSTRACT

Provided herein is a method for detecting at least two distinct oligonucleotides of equal length in parallel from one biological sample, comprising the steps of providing a biological sample containing or suspected of containing oligonucleotides of interest; forming a hybridization mixture using at least two fluorescently labelled detection molecules with different surface charges; separating the detection molecules hybridized to the oligonucleotides by anion exchange HPLC; and detecting the hybridized detection molecule-oligonucleotide moieties by quantitative fluorescence readout. In a further aspect, a kit comprising at least two detection molecules is provided. In another aspect, provided herein is the use of at least two detection molecules with different surface charges for quantitatively detecting at least two distinct oligonucleotides of equal length in parallel from one biological sample.

19 Claims, 8 Drawing Sheets

Figure 1:
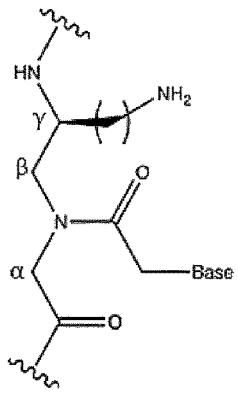
Figure 1:
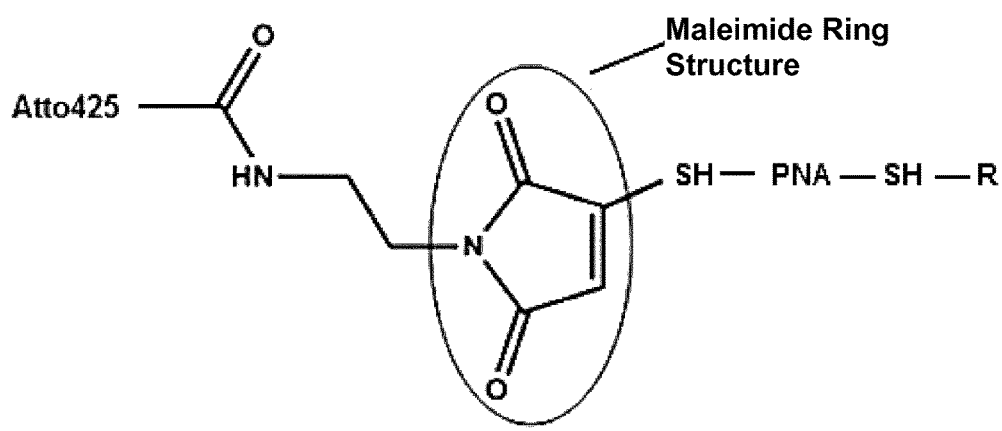
Figure 1:
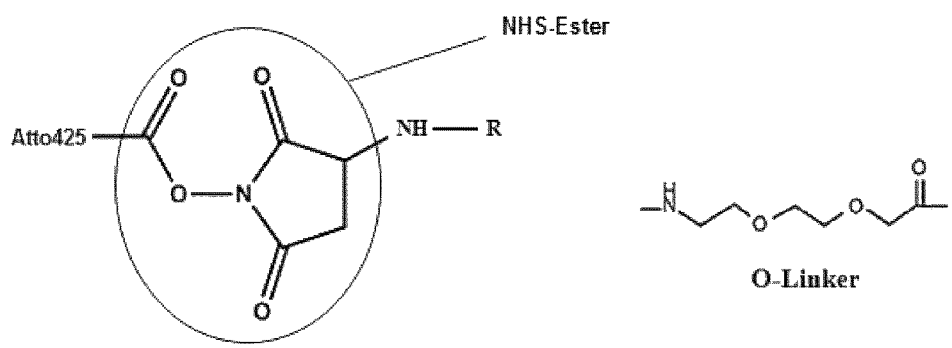

Specification includes a Sequence Listing.

(56) References Cited

OTHER PUBLICATIONS

Batkai, Sandor et al., "Analytical approaches in microRNA therapeutics", Journal of Chromatography B, 2014, vol. 964, pp. 146-152.

Demidov, Vadim et al., "Stability of peptide nucleic acids in human serum and cellular extracts", Biochemical Pharmacology, Sep. 15, 1994, vol. 48, No. 6, pp. 1310-1313.

Dias, Nathalie et al., "Antisense Oligonucleotides: Basic Concepts and mechanisms", Molecular Cancer Therapeutics, Mar. 2002, vol. 1, pp. 347-355.

Egholm, Michael et al., "PNA hybridizes to complementary oligonucleotides obeying the Watson-Crick hydrogen-bonding rules", Nature, Oct. 7, 1993, vol. 365, pp. 566-568.

Farazi, Thalia A. et al., "microRNAs in Human Cancer", Adv. Exp. Med. Biol., 2013, vol. 774, pp. 1-20.

Janowski, Bethany A. et al., "Activating gene expression in mammalian cells with promoter-targeted duplex RNAs", Nature Chemical Biology, Mar. 2007, vol. 3, No. 3, pp. 166-173.

Kataoka, Masaharu et al., "Non-Coding RNAs Including miRNAs and lncRNAs in Cardiovascular Biology and Disease", Cell, 2014, vol. 3, pp. 883-898.

Kumarswamy, Regalla et al., "Regulation and function of miRNA-21 in health and disease", RNA Biology, 2011, vol. 8, No. 5, pp. 706-713.

Li, Long-Cheng et al., "Small dsRNAs induce transcriptional activation in human cells", Proc. Natl. Acad. Sci USA, Nov. 14, 2006, vol. 103, No. 46, pp. 17337-17342.

Lorenzen, Johan M. et al., "Circulating miR-210 Predicts Survival in Critically Ill Patients with Acute Kidney Injury", Clin. J. Am. Soc. Nephrol, Jul. 2011, vol. 6, pp. 1540-1546.

Summerton, James et al., "Morpholino Antisense Oligomers: Design, Preparation, and Properties", Antisense & Nucleic Acid Drug Development, 1997, vol. 7, pp. 187-195.

Tataurov, Andrey V. et al., "Predicting ultraviolet spectrum of single stranded and double stranded deoxyribonucleic acids", Biophysical Chemistry, 2008, vol. 133, pp. 66-70.

Calabretta, Alessandro et al., "Arginine-based PNA microarrays for APOE genotyping," Molecular Biosystems, vol. 5, No. 11, Jan. 1, 2009, pp. 1323.

International Search Report and Written Opinion issued in PCT/EP2016/054450, dated May 6, 2016.

Germini, Andrea et al., "Polymerase chain reaction coupled with peptide nucleic acid high-performance liquid chromatography for the sensitive detection of traces of potentially allergenic hazelnut in foodstuffs," European Food Research and Technology; Zeitschrift Für Lebensmitteluntersuchung Uno—Forschung A, Springer, Berlin, DE, vol. 220, No. 5-6, May 1, 2005, pp. 619-624.

Lesignoli, Francesca et al., "Recognition and strand displacement of DNA oligonucleotides by peptide nucleic acids (PNAs)—High-performance ion-exchange chromatographic analysis," Journal of Chromatography, Elsevier Science Publishers B.V, NL, vol. 922, No. 1-2, Jul. 13, 2001, pp. 177-185.

Rossi, Stefano et al., "Identification of PCR-amplified genetically modified organisms (GMOs) DNA by peptide nucleic acid (PNA) probes in anion-exchange chromatographic analysis," Journal of Agricultural and Food Chemistry, American Chemical Society, US, vol. 55, No. 7, Apr. 4, 2007, pp. 2509-2516.

```
                             SEQUENCE LISTING

<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: modified peptide nucleic acid (SEQ ID NO: 1)
<220> FEATURE:
<221> NAME/KEY: misc_binding
<222> LOCATION: (1)..(1)
<223> OTHER INFORMATION: site which covalently binds another moiety in
      form of Atto425 coupled via cysteine and two O-linkers
<220> FEATURE:
<221> NAME/KEY: misc_binding
<222> LOCATION: (19)..(19)
<223> OTHER INFORMATION: site which covalently binds another moiety in
      form of Atto425 coupled via cysteine and one O-linker

<400> SEQUENCE: 1
gccaatattt acgtgctgc                                                  19

<210> SEQ ID NO 2
<211> LENGTH: 19
<212> TYPE: DNA
<213> ORGANISM: Artificial Sequence
<220> FEATURE:
<223> OTHER INFORMATION: modified peptide nucleic acid (SEQ ID NO: 2)
<220> FEATURE:
<221> NAME/KEY: misc_binding
<222> LOCATION: (1)..(1)
<223> OTHER INFORMATION: site which covalently binds another moiety in
      form of Atto425 coupled via cysteine and three glutamic acids
<220> FEATURE:
<221> NAME/KEY: misc_binding
<222> LOCATION: (19)..(19)
<223> OTHER INFORMATION: site which covalently binds another moiety in
      form of Atto425 coupled via cysteine and three glutamic acids

<400> SEQUENCE: 2
gccaatattt acgtgctgc                                                  19

<210> SEQ ID NO 3
<211> LENGTH: 19
<212> TYPE: DNA
<213> ORGANISM: Artificial Sequence
<220> FEATURE:
<223> OTHER INFORMATION: modified peptide nucleic acid (SEQ ID NO: 3)
<220> FEATURE:
<221> NAME/KEY: misc_binding
<222> LOCATION: (1)..(1)
<223> OTHER INFORMATION: site which covalently binds another moiety in
      form of Atto425 coupled via cysteine and two O-linkers
<220> FEATURE:
<221> NAME/KEY: misc_binding
<222> LOCATION: (3)..(3)
<223> OTHER INFORMATION: site with lysine gamma modification
<220> FEATURE:
<221> NAME/KEY: misc_binding
<222> LOCATION: (6)..(6)
<223> OTHER INFORMATION: site with lysine gamma modification
<220> FEATURE:
<221> NAME/KEY: misc_binding
<222> LOCATION: (9)..(9)
<223> OTHER INFORMATION: site with lysine gamma modification
```

```
<220> FEATURE:
<221> NAME/KEY: misc_binding
<222> LOCATION: (12)..(12)
<223> OTHER INFORMATION: site with lysine gamma modification
<220> FEATURE:
<221> NAME/KEY: misc_binding
<222> LOCATION: (15)..(15)
<223> OTHER INFORMATION: site with lysine gamma modification
<220> FEATURE:
<221> NAME/KEY: misc_binding
<222> LOCATION: (19)..(19)
<223> OTHER INFORMATION: site which covalently binds another moiety in
      form of Atto425 coupled via cysteine and one O-linker

<400> SEQUENCE: 3
gccaatattt acgtgctgc                                                  19

<210> SEQ ID NO 4
<211> LENGTH: 17
<212> TYPE: DNA
<213> ORGANISM: Artificial Sequence
<220> FEATURE:
<223> OTHER INFORMATION: modified peptide nucleic acid (SEQ ID NO: 4)
<220> FEATURE:
<221> NAME/KEY: misc_binding
<222> LOCATION: (1)..(1)
<223> OTHER INFORMATION: site which covalently binds another moiety in
      form of Atto425 coupled via two O-linkers
<220> FEATURE:
<221> NAME/KEY: misc_binding
<222> LOCATION: (17)..(17)
<223> OTHER INFORMATION: site which covalently binds another moiety in
      form of Atto425 coupled via lysine and one O-linker

<400> SEQUENCE: 4
tcgccctctc aacccag                                                    17

<210> SEQ ID NO 5
<211> LENGTH: 19
<212> TYPE: DNA
<213> ORGANISM: Artificial Sequence
<220> FEATURE:
<223> OTHER INFORMATION: modified peptide nucleic acid (SEQ ID NO: 5)
<220> FEATURE:
<221> NAME/KEY: misc_binding
<222> LOCATION: (1)..(1)
<223> OTHER INFORMATION: site which covalently binds another moiety in
      form of Atto425 coupled via one O-linker and two glutamic acids
<220> FEATURE:
<221> NAME/KEY: misc_binding
<222> LOCATION: (19)..(19)
<223> OTHER INFORMATION: site which covalently binds another moiety in
      form of Atto425 coupled via lysine and two glutamic acids

<400> SEQUENCE: 5
gccaatattt acgtgctgc                                                  19

<210> SEQ ID NO 6
<211> LENGTH: 17
<212> TYPE: DNA
<213> ORGANISM: Artificial Sequence
<220> FEATURE:
<223> OTHER INFORMATION: modified peptide nucleic acid (SEQ ID NO: 6)
<220> FEATURE:
<221> NAME/KEY: misc_binding
<222> LOCATION: (1)..(1)
<223> OTHER INFORMATION: site which covalently binds another moiety in
      form of Atto425 coupled via one O-linker and four glutamic acids
<220> FEATURE:
<221> NAME/KEY: misc_binding
<222> LOCATION: (17)..(17)
<223> OTHER INFORMATION: site which covalently binds another moiety in
      form of Atto425 coupled via lysine and four glutamic acids
```

```
<400> SEQUENCE: 6
cagtgtgcgg tgggcag                                                      17

<210> SEQ ID NO 7
<211> LENGTH: 22
<212> TYPE: RNA
<213> ORGANISM: Homo sapiens

<400> SEQUENCE: 7
uagcagcacg uaaauauugg cg                                                22

<210> SEQ ID NO 8
<211> LENGTH: 22
<212> TYPE: RNA
<213> ORGANISM: Homo sapiens

<400> SEQUENCE: 8
agccccugcc caccgcacac ug                                                22

<210> SEQ ID NO 9
<211> LENGTH: 22
<212> TYPE: RNA
<213> ORGANISM: Homo sapiens

<400> SEQUENCE: 9
aaaagcuggg uugagagggc ga                                                22
```

SIMULTANEOUS DETECTION OF OLIGONUCLEOTIDES, A KIT AND A USE RELATED THERETO

CROSS-REFERENCE TO RELATED APPLICATIONS

The present application is a U.S. National Phase of PCT/EP2016/054450, filed Mar. 2, 2016, which claims priority to EP 15000588.2, filed Mar. 2, 2015, the disclosures of each of which are incorporated by reference herein in their entireties.

SEQUENCE LISTING

This application incorporates by reference a "Sequence Listing" (provided herewith); this Sequence Listing is incorporated by reference in its entirety herein.

DNA and RNA molecules play an important role in gene expression in a variety of organisms. For example, small RNAs were recently discovered as important regulators of post-transcriptional gene expression, in particular gene silencing, with impact on both physiological and pathological processes in living cells. Since then, a variety of short RNAs have been found to be abundant classes of gene regulators in plants, animals, and DNA viruses, and short RNAs of different origin and function have been identified in a variety of organisms from fission yeast to human. Among them, miRNAs are the most abundant type of small regulatory RNAs in plants and animal. To date, more than 20.000 different miRNAs have been identified by cloning and sequencing (see, for example, miRBase: the microRNA registry database at http://www.mirbase.org/, Sanger Institute, UK). In general, miRNAs are characterized by a length of 21-25 nucleotides (nts) and implicated into the regulation of protein expression by a mechanism in which complementary base pairs are formed between the miRNA and its target mRNA. This process leads to the inhibition of protein translation and, depending on the degree of sequence complementary between the miRNA and its target site, also to the degradation of the mRNA transcript (for review see, e.g., Bartel D P, Cell 2009, 136(2): 215-233).

Altered miRNA expression has been implicated to contribute to human diseases, in particular to cancer, based on the finding that malignant tumours and tumour cell lines reveal deregulated miRNA expression profiles in comparison to normal tissues (for review see, e.g., Farazi et al., 2013, Adv. Exp. Med. Biol 774: 1-20). That is, a global decrease in miRNA levels has been observed in human cancers, indicating that small regulatory RNAs may have an intrinsic function in tumour suppression. Since there is a global down regulation of miRNAs in tumours, the expression profile of miRNAs may reflect the origin and differentiation state of this disease. In a similar manner, other diseases are characterized by either up and/or down regulated levels of endogenously expressed miRNAs such as, for example, the small regulatory RNA miRNA-21 which expression has been found to be deregulated in almost all type of cancers but to also play a crucial role in diverse other biological processes including development, cardiovascular and pulmonary diseases and inflammation (for review see, e.g., Kumarswamy et al., 2011, RNA Biology 8: 5, 706-713, and Kataoka and Wang, Cell 2014, 3: 883-898). Moreover, renal failure has been shown to be characterized by a different expression pattern of the small regulatory RNAs miRNA-320 and miR-210 (Lorenzen J. M. et al, Clin. J. Am. Soc. Nephrol, 6: 1540-1546).

Synthetic molecules that can bind with high sequence specificity to a chosen target gene sequence are of major interest in medical and biotechnological contexts since they show promise for the development of gene therapeutic agents and diagnostic devices. That is, oligonucleotides of known sequence, for example, are commonly used in a wide variety of chemical and biological applications and have gained increasing importance in diagnostic and therapeutic applications.

The analysis of oligonucleotides used as therapeutic agents from physiological samples including the analysis of small regulatory RNAs in form of, e.g., miRNA expression profiles has already developed to be an important tool in medical diagnostic. MicroRNAs are readily detectable oligonucleotides that are currently employed as biomarkers in a wide range of diseases. Highly sensitive detection systems for the quantitative analysing of particular classes of small regulatory oligonucleotides are thus an important tool for state-of-the art medical diagnostics. Current high-throughput detection approaches, however, largely rely on methods employing quantitative real-time polymerase chain reaction (RT-PCR). RT-PCR enables both the detection and quantification in form of absolute number of copies as well as in form of relative amounts. These methods, however, need an intensive sample preparation including prior amplification of the target sequence and are time consuming and expensive.

Ion-exchange chromatography in combination with either UV absorbance or fluorescent detection is so far mainly been used for analyzing the degree of purity of synthetic oligonucleotides, or for detecting oligonucleotide modifications. Here, oligonucleotides are separated on a positive stationary phase by the number of negative phosphodiester backbone charges which are defined by the length of their backbone. Ion-exchange chromatography coupled with either UV detection or fluorescent readout has further been described in the context of analyzing the pharmacokinetics of therapeutic oligonucleotides (WO 2010/043512 A1, for review see, e.g., Batkai and Thum, 2014, Journal of Chromatography B, 964: 146-152).

The expanding small regulatory oligonucleotide field is currently facing many analytical changes, both at the molecular as well as at large-scale diagnostic level. The provision of highly sensitive, reliable and quick detection methods for absolute quantification and normalization in the context of high-throughput screenings is, therefore, a major issue of utmost importance in the field of medical research, diagnostic and therapy.

Hence, there is always a need for an improved method for quantitatively detecting target oligonucleotides of interest in parallel from one sample, including the analysis of the expression pattern of small regulatory RNAs such as miR-NAs with equal length but different identity, or other therapeutic oligonucleotides.

In the context of the present invention, it has been found that oligonucleotides of different sequence but equal length can quantitatively be detected and thereby analyzed in parallel by a method employing complementary detection molecules in combination with anion-exchange high performance liquid chromatography (AEX-HPLC), wherein the detection molecules are fluorescently labeled and chemically modified to reveal different overall surface charges. That is, while oligonucleotides of equal length reveal similar elution profiles after binding to a positively charged stationary phase due to their similar negative backbone charges, the annealing of complementary detection molecules with different surface charges significantly alters the target oligonucleotides overall surface charges and, thereby, enables an improved resolution and allows for the otherwise impossible separation of the respective target oligonucleotides due to their altered binding affinities after hybridization to their respective detection molecule. The method of the present invention is thus particularly suitable to detect more than one species of oligonucleotides in parallel in one sample, in particular when the oligonucleotides are of identical or similar length which would normally challenge or impede their separation by chromatographic methods. Therefore, the method of the present invention is particularly suitable for detecting multiple small regulatory RNAs or DNA molecules of equal length in one approach, including, e.g., in the context of high-throughput quantification of multiple miRNAs or small therapeutic RNAs in parallel from one biological sample of interest.

Accordingly, in a first aspect, the present invention relates to a method for quantitatively detecting at least two distinct oligonucleotides of equal length in parallel from one biological sample, said method comprising the steps of a) providing a biological sample containing or suspected of containing the at least two distinct oligonucleotides of equal length;

b) forming a hybridization mixture by contacting the biological sample with at least two detection molecules complementary to the at least two distinct oligonucleotides of equal length, wherein the detection molecules are each labelled with at least one fluorescent moiety, and wherein the detection molecules have different surface charges;

c) separating the detection molecules hybridized to the at least two distinct oligonucleotides of equal length from the moiety of non-hybridized detection molecules by anion exchange high performance liquid chromatography (AEX-HPLC);

d) detecting the hybridized detection molecule-oligonucleotide moieties by means of quantitative fluorescence readout.

The term "oligonucleotide" as used in the context of the present invention generally refers to an oligomer or polymer composed of either deoxyribonucleotides (DNA) or ribonucleotides (RNA), preferably to an oligomer or polymer composed of ribonucleotides (RNA). Hence, in the context of the present invention, the oligonucleotides of interest are preferably RNA molecules in form of RNA oligonucleotides, including, but not limited to, small regulatory RNAs such as miRNAs and siRNAs. Equally preferred is that the oligonucleotides of the present invention are DNA molecules in form of DNA oligonucleotides, including, but not limited to, all kind of synthetically designed and/or manufactured DNA oligonucleotides such as, for example, decoy oligonucleotides. In principle, oligonucleotides according to the present invention include all kind of structures composed of a nucleobase (i.e. a nitrogenous base), a five-carbon sugar which may be either a ribose, a 2'-deoxyribose, or any derivative thereof, and a phosphate group. The nucleobase and the sugar constitute a unit referred to as a nucleoside. The phosphate groups may form bonds with the 2, 3, or the 5 carbon, in particular with the 3 and 5 carbon of the sugar. A ribonucleotide contains a ribose as a sugar moiety, while a deoxyribonucleotide contains a deoxyribose as a sugar moiety. Nucleotides can contain either a purine or a pyrimidine base. Accordingly, the oligonucleotides according to the present invention, constituted by either ribonucleotides or deoxyribonucleotides or by any combination thereof, may further include one or more modified nucleotide(s). Optionally, oligonucleotides may further comprise only modified nucleotides. Ribo- and deoxyforms of modified nucleotides may, e.g., include, but are not limited to, 5-propynyl-uridine, 5-propynyl-cytidine, 5-methyl-cytidine, 2-amino-adenosine, 4-thiouridine, 5-iodouridine, N6-methyl-adenosine, 5-fluorouridine, inosine, 7-propynyl-8-aza-7-deazapurine and 7-halo-8-aza-7-deazapurine nucleosides. The oligonucleotides as referred to in the context of the present invention may further comprise backbone modifications such as, e.g., 2'-O-methyl (2'-OMe) RNA or 2'-fluoro (2'-F) RNA. Optionally, the oligonucleotides of the present invention may also or instead comprise one or more modification(s) on the phosphate backbone such as, e.g., phosphorothioates or methyl phosphonates, which are known to increase the stability against nucleases.

The term "distinct oligonucleotides of equal length" as used herein means single stranded or double stranded oligonucleotide molecules of identical or similar length, i.e. oligonucleotides which are composed of either an identical or similar number of nucleotides. The term "equal length" preferably defines that the oligonucleotides of interest have an identical length. In this case the oligonucleotides of interest are composed of an identical number of nucleotides. Equally preferred, however, is that the oligonucleotides of interest have a similar length, i.e. a length which slightly differs from each other. An "equal length" according to the present invention, thereby, also includes that the length of the respective oligonucleotides vary from each other by a couple of nucleotides, preferably by maximal five, four, three or two nucleotides. More preferably, the at least two distinct oligonucleotides of interest vary by only one nucleotide in length.

That is, in a preferred embodiment, the at least two oligonucleotides to be detected by the method of the present invention may have a similar length which varies by 5 nucleotides, or, alternatively, by 4 nucleotides, or, alternatively by 3 nucleotides, or, alternatively, by 2 nucleotides. More preferably, the oligonucleotides of interest may have a similar length which varies by only one nucleotide. In those cases in which more than two distinct oligonucleotides of interest are detected in parallel from one sample, for example, in cases in which three, four, five, six, seven, eight, nine, ten or even more oligonucleotides of equal length are detected in parallel from one sample, the oligonucleotides to be detected may be of either identical or similar length, or both, as defined by any of combinations or alternatives as described above.

Preferably, distinct oligonucleotides of equal length according to the present invention are oligonucleotides of different sequence, but composed of an identical number of nucleotides. Oligonucleotides of similar length which differ in length by only a small number of nucleotides, preferably by a difference of no more than 5 nucleotides in length, are equally preferred. The definition "distinct oligonucleotides of equal length" as used herein does further not exclude that the oligonucleotides of interest may include, comprise or encompass one or more identical or different chemical modification(s). The chemical modifications may be identical or different with respect to both number and/or identity.

Generally, in the context of the present invention, the oligonucleotides to be detected may have a total length of from 10 to 50 nucleotides, or from 12 to 40 nucleotides, or from 12 to 30 nucleotides, or preferably a length of from 10 to 25 nucleotides. Equally preferred is that the oligonucleotides of interest may have a length in the range of 15 to 30 nucleotides, more preferably in the range of 18 to 25 nucleotides, most preferably in the range of 20 to 22 nucleotides. However, it is evident to the skilled person that the above upper and lower limits may also be combined in order to arrive at different ranges. Moreover, the sample of the invention containing the oligonucleotides of interest may contain a population of oligonucleotide molecules with such variable lengths. That is, the sample provided in the context of the present invention may comprise oligonucleotides of the same length, or may comprise oligonucleotides of different length, or both, including, but not limited to, precursor and mature forms of an oligonucleotide of interest such as, for example, a miRNA and its precursor, or long non-coding RNAs. The presence of oligonucleotides of different length, however, does not impair the quantitative detection of oligonucleotides of equal length by the method of the present invention.

Hence, in a preferred embodiment, the at least two distinct oligonucleotides have a length of from 10 to 50 nucleotides, preferably of from 12 to 40 nucleotides, more preferably of from 18 to 30 nucleotides.

The oligonucleotides to be detected in the context of the present invention can further derive from all kind of natural, non-natural or artificial sources including, but not limited to, viral, bacterial and eukaryotic DNA or RNA. Alternatively, the oligonucleotides of interest can derive from synthetic sources including those that are manufactured and synthesized for use in research, as diagnostic or as therapeutic agents. The term "synthesizing" as used herein preferably refers to the manufacture of DNA or RNA oligonucleotides by means of chemical synthesis including, but not limited to, the use of automated DNA and/or RNA synthesizers and/or phosphoramidite chemistry. Automated DNA or RNA synthesizers are routinely used by the person skilled in the art and are commercially available from diverse suppliers such as, e.g., Applied Biosystems (Darmstadt, Germany), Biolytic (Newark, Calif., USA), GE Healthcare or BioAutomation (Plano, Tex., USA).

The feature "providing a biological sample" as used in the context of the present invention refers to all kind of procedures suitable to prepare a composition containing the at least two distinct oligonucleotides of interest or, alternatively, a population of oligonucleotides to be detected for further analysis. These procedures include, but are not limited to, standard biochemical and/or cell biological procedures suitable for the preparation of a cell or tissue extract, wherein the cells and/or tissues may be derived from any kind of organism containing the at least two oligonucleotides of interest. For example, a sample according to the present invention may be a cell extract or a tissue extract encompassing purified total RNA and/or size fractionated total RNA, for example, derived from a cell or cells grown in cell culture or obtained from an organism by dissection and/or surgery. In particular, a biological sample according to the present invention may be obtained from one or more tissue(s) of one or more patient(s) or any kind of living subject. Provision of a biological sample from a cell, from a cell extract or from a tissue may include one or more biochemical purification step such as, e.g., centrifugation and/or fractionation, cell lysis by means of mechanical or chemical disruption steps including, for example, multiple freezing and/or thawing cycles, salt treatment(s), phenol-chloroform extraction, sodium dodecyl sulfate (SOS) treatment and proteinase K digestion. Optionally, providing a biological sample according to the present invention may further include the removal of large RNA, such as abundant ribosomal rRNA, by precipitating in the presence of polyethylene or salt, or the removal of interfering sodium dodecyl sulfate (SOS) by precipitation in the presence of salt, preferably in the presence of potassium chloride solution.

Methods of purifying total RNA from a cell and/or a tissue are well known to a person skilled in the art and include, e.g., standard procedures such as the use of guanidinium thiocyanate-acidic phenol-chloroform extraction (e.g. TRIZOL®, INVITROGEN®, USA).

In the context of the present invention, it is, however, equally preferred that the biological sample is provided without any of the herein described precipitation and/or purification steps. That is, in a preferred embodiment, the biological sample of the present invention may be subjected only to a proteinase K digestion in the presence of SDS. After digestion of the biological sample in the presence of SDS, the interfering sodium dodecyl sulfate (SDS) may be removed by a subsequent precipitation step in the presence of salt, preferably in the presence of potassium ions. Equally preferred, however, is that the biological sample is provided or processed in the presence of proteinase K, preferably by enzymatic proteinase K digestion, in the absence of SDS. In this case, all precipitation steps to eliminate the interfering SDS may be omitted.

Moreover, the biological sample according to the present invention may further comprise or be complemented by one or more synthetic molecule(s) such as, for example, synthetic oligonucleotide molecule(s) of known concentration(s) and/or of known molecular weight(s) which may serve as an internal standard for quantification and/or for quantitative fluorescent readout. The synthetic molecules which may be used as an internal standard are either provided in form of a mixture of molecules with different concentrations and/or with different molecular weights, or in form of various dilution series. In all embodiments, the synthetic oligonucleotide molecules are preferably fluorescently labelled to allow for a direct quantitative fluorescent readout and are treated in the same manner as the biological sample of interest. Suitable molecules which may be serve as an internal standard in the context of the present application may include, but are not limited to, synthetic oligonucleotides which correspond to the target sequence(s) of the at least two oligonucleotides of interest, or corresponding to fragments thereof.

Alternatively, the biological sample may contain at least three, preferably five different concentrations of a fluorescently labeled synthetic molecule which sequence corresponds to different lengths of the sequence of the target oligonucleotide to be detected. For example, for detecting a target oligonucleotide of 20 nucleotides in length, fluorescently labeled synthetic oligonucleotide molecules with a length of 8, 11 and 14 nucleotides, respectively, may be used as an internal standard for quantification. Alternatively, the fluorescently labeled oligonucleotides may have different lengths which extend the original length of the target oligonucleotide(s) to be detected. For example, for detecting a target oligonucleotide of 20 nucleotides in length, fluorescently labeled oligonucleotide molecules with a length of 24, 28 and 32 nucleotides, respectively, may be used as an internal standard for a quantitative fluorescent readout. Here, the fluorescently labeled oligonucleotides may correspond to the sequence of the target oligonucleotides to be detected and may encompass additional, preferably artificially designed, nucleotide extensions which do not correspond to the target sequence(s) of interest.

Generally, in the context of the present invention, the fluorescently labeled oligonucleotides used for internal quantification are preferably synthetically synthesized. Moreover, the fluorescently labeled oligonucleotides used as an internal standard will preferably be hybridized to their respective detection molecule(s) in the same manner as the target oligonucleotides of interest before they are separated via anion exchange HPLC chromatography. That is, quantification by the use of internal standards as described herein relies on the formation, elution and separation of duplexes via anion exchange high performance liquid chromatography (AEX-HPLC), wherein the duplexes of the internal standard comprise fluorescently labeled oligonucleotides hybridized to detection molecules of complementary sequence. More preferably, for a quantitative readout, the fluorescently labelled oligonucleotides are separated and eluted from the anion exchange column together with the biological sample of interest in one experimental set up, in particular as part of the same AEX-HPLC column run. In this set up, the quantitative fluorescence readout relies on the comparison of the different peak heights and/or different peak areas generated by the oligonucleotide duplexes of the internal standard with the heights and/or the areas of the elution peaks generated by the respective detection molecule-oligonucleotide moieties of interest. Quantitative fluorescence readout using internal standard is well know to the skilled person and routinely applied in laboratory practice, and software programs are commercially available for calculating, comparing, integrating and/or quantifying elution peak heights and/or peak areas on a quantitative basis (e.g. ThermoFisher, Waters, Shimadzu, Agilent, USA).

Examples of biological samples according to the present invention include, but are not limited to, e.g., blood, plasma, urine, feces, liver, lung, spinal liquid or any other cell, tissue and/or biopsy sample obtained from an individual, preferably obtained from an individual with a particular disease, preferably with a renal disease, more preferably with kidney injury.

Accordingly, in a preferred embodiment, the biological sample is a sample obtained form one or more individual(s), including non-human and human subjects, preferably in form of a biopsy sample, more preferably in form of cells, tissue or liquid. Equally preferred, however, is that the biological sample is derived from an experimental set up or from an in vitro or an in vivo experiment such as, for example, biological or biochemical assays, molecular genetic assays, cell culture assays or mice. The biological sample of the present invention may further be selected from the group consisting of blood, plasma, urine, feces, and spinal liquid samples, including tissue(s) and/or cell(s) samples derived from liver, lung, kidney, breast, prostate, heart or brain. In a preferred embodiment, the biological sample is a plasma sample.

In the context of the present invention, the term "detection molecule" generally means any kind of molecule which is suitable to anneal to the target oligonucleotide sequence(s) of interest by complementary base pairing, thereby forming a duplex of two complementary strands. Moreover, the detection molecule according to the present invention shall contain a fluorescent moiety which allows for the detection, analysis and/or visualization of the at least two oligonucleotides of interest upon hybridization. In general, the at least two oligonucleotides of interest are not fluorescently labeled. Suitable detection molecules according to the present invention include, but are not limited to, all kinds of synthetically designed and/or manufactures molecules with neutral net charge such as, for example, peptide nucleic acids (PNAs), phosphorodiamidate morpholino oligomers (PMOs) and ugimers. That is, the detection molecule of the present invention is preferably characterized by a neutral backbone charge, in particular by lacking any charged ion groups such as, for example, negatively charged phosphate groups.

Accordingly, in a preferred embodiment, the detection molecule is selected from the group consisting of peptide nucleic acids (PNAs), phosphorodiamidate morpholino oligomers (PMOs) and ugimers.

The detection molecule of the present invention is generally synthesized to match to a nucleotide sequence of interest and can be used to detect, analyse, and/or visualize said nucleotide sequence on a molecular level. It will be evident to the skilled person that the detection molecule of the present invention has a length suitable to provide the required specificity for annealing with its target molecule. The detection molecule according to the present invention is composed of several nucleotides, preferably of at least 10, more preferably of at least 15 nucleotides, and preferably comprises at least one fluorescent moiety in form of a fluorescent label.

In a preferred embodiment, the detection molecules employed in the context of the present invention have a length of from 10 to 30 nucleotides, preferably a length of from 10 to 20 nucleotides, more preferably a length of from 15 to 20 nucleotides.

The term "peptide nucleic acid (PNA)" as used herein generally refers to any kind of nucleic acid analogue in which the sugar phosphate backbone of natural nucleic acid has been replaced by a synthetic peptide backbone usually formed by repeating N-(2-aminoethyl)-glycine units which lack any charged phosphate groups. Optionally, the peptide nucleic acid may also comprise any kind of suitable non-glycine unit(s) and/or linking reagent(s) which may allow for or facilitate the incorporation of one or more additional label(s) or chemical modifications. In general, peptide nucleic acids are customer designed and chemically synthesized. That is, in the context of the present invention, the peptide nucleic acids are customer designed to match to the respective oligonucleotide of interest which preferably means that the sequence of the peptide nucleic acid is complementary to the target oligonucleotide sequence of interest to be detected. Peptide nucleic acids are well known to the skilled person and commercially available from a variety of suppliers, including for example, BioSynthesis Inc., USA or Panagene (South Korea).

Phosphorodiamidate morpholino oligomers (PMOs) are non-ionic DNA analogs and thereby a distinct class of oligonucleotide analogs which may be employed as detection molecules in the context of the present invention. Their non-ionic character combined with resistance to degradation makes them suitable for use as detection molecules for quantitatively detecting oligonucleotides of equal length according the present invention. Hence, in the context of the present invention, phosphorodiamidate morpholino oligomers (PMOs) can be used as an equally suitable alternative to peptide nucleic acids, since they can be rationally designed based on target gene sequence data. Phosphorodiamidate morpholino oligomers (PMOs) are well known in the art (see, e.g., Summerton J, Weller D (1997), Antisense Nucleic Acid Drug Dev, 7: 187-95) and are commercially available from a variety of company including, for example, Gene Tools, LLC, USA.

Ugimers are a further alternative to peptide nucleic acids which can be used as a detection molecule in the context of the present invention. Ugimers are based on the non-natural peptide nucleic acid (PNA) backbone and therefore possess all the advantages of PNAs, including strong steric block efficacy, high target specificity, high stability, low toxicity, and a low risk of provoking an immune response. Ugimers can be modified by the integration of particular side chains along the PNA backbone which may considerably improves their solubility in water and which allows for a selective modulation of their overall surface charges including the coupling of fluorescent moieties for fluorescent detection. Ugimers are, for example, commercially available from the company Ugichem GmbH, Innsbruck, Austria.

The detection molecule of the present invention may preferably, but not necessarily, be designed as to reveal a complementarity to its oligonucleotide target sequence of 100%. The detection molecule may also be designed as to reveal less than 100% complementarity to the oligonucleotide target sequence, if considered appropriate. The complementarity between the detection molecule and its oligonucleotide target sequence of interest, however, has to be to such an extent as to provide specific binding to and, consequently, fluorescent detection of the oligonucleotide(s) of interest. The degree of complementarity is to be established on a case to case basis depend on the respective target molecule and the respective experimental setup. The design of detection molecules, such as peptide nucleic acids, is a routine method for the skilled person and may be facilitated by bioinformatics approaches. With the increasing numbers of cloned genes, peptide nucleic acids, ugimers or PMOs can easily be designed based on any published cDNA sequence and/or gene bank entry. Databases with genomic sequences from diverse organisms are known to the person skilled in the art and include, for example, all public databases from the NCBI (National Center of Biological Information, USA or the microRNA registry database).

The detection molecules employed in the context of the present invention are further characterized by different overall surface charges. The term "different surface charge(s)" as used herein generally means that the overall surface charge of the at least two detection molecules employed in the context of the present invention is different from each other. In particular, in the context of the present invention, different surface charge(s) means that the detection molecules such as, for example, the peptide nucleic acids, are either negatively, positively or neutrally charged to such a distinguishable extent that they are able to alter the binding affinity of equally charged target oligonucleotide molecules during anion exchange chromatography. In particular, the different surface charge(s) of the detection molecules employed in the context of the present invention enable, upon annealing to their respective target sequence, that target oligonucleotides of equal length can be separated by only one anion-exchange chromatography step from one biological sample in parallel at high resolution. In the context of the present invention, the different surface charge(s) of the at least two detection molecules are a result of incorporated chemical modification(s), such as, for example, the incorporation of either positively and/or negatively charged additional amino acids and/or other functional groups which alter the overall surface charge of the respective molecule. This difference is to be maintained after hybridizing to the respective target sequence. In the context of the present invention, it is envisaged that the number and/or the identity of the chemical modification(s) to be incorporated into the detection molecule, i.e. the design of the respective overall surface charge(s), will be carried out in accordance with the structural characteristics and requirements of the particular target molecule(s) of interest. That is, the surface charge of the respective target molecule has to be taken into account when designing the surface charge of the chemically modified detection molecule. Chemical modifications which may alter the overall surface charge of a detection molecule, such as, for example, a peptide nucleic acid or an ugimer, include, but are not limited to, any kind of amino acid with a positively or negatively charged side chain, as well as other positively or negatively charged chemical linkers and/or molecules which can be incorporated into the peptide nucleic acid's or the ugimer's backbone without altering the molecule's function to specifically anneal with and bind to its respective target sequence. Preferably, the chemical modification(s) is/are incorporated at either end(s) of the detection molecule, such as, for example, at either the N'- or the C'-terminal end of the peptide nucleic acid, more preferably at both the N'- and the C' terminal end. Equally preferred, however, is that the chemical modification(s) is/are incorporated into the backbone of the peptide nucleic acid or the ugimer, preferably wherein the chemical modification is linked to the gamma position of the N-(2-aminoethyl)-glycine backbone. These kinds of chemically modified PNAs are known as so called gamma-PNA. Both peptide nucleic acids and ugimers are equally suitable for being modified by the introduction of additional surface charges into their backbone, in particular linked to gamma positions. Chemically modified peptide nucleic acids or chemically modified ugimers are commercially available from diverse sources and may, for example, be purchased from Paranege (South Korea) or Ugichem GmbH, Austria.

The term "complementary to" as referred to in the context of the present invention generally means the capability of a polynucleotide to specifically bind to a target sequence of interest by means of complementary base pairing. Complementary base pairs are formed between two nucleotide molecules (which may or may not include one or more modification(s)) that are complementary to each other. In the context of the present invention, complementary base pairs which are, e.g., formed between the detection molecule and the oligonucleotide molecule of interest, may include all kind of canonical or non-canonical base pairs, including, but not limited to, Watson-Crick A-U, Watson-Crick A-T, Watson-Crick G-C, G-U Wobble base pairs, A-U and A-C reverse Hoogsteen base pairs, or purine-purine and pyrimidine-pyrimidine base pairs such as sheared G-A base pairs or G-A imino base pairs. Preferably, the term "complementary to" refer to canonical base pairs.

The term "hybridizing" or "hybridization" as used herein generally refers to the annealing of two complementary oligonucleotide strands, and in particular means the annealing of the at least two detection molecules to their complementary target oligonucleotides. Successful hybridization depends on a variety of factors, including temperature, salt concentrations, and/or pH. The optimal temperature for hybridization is preferably in the range of 5-15° C. below the $T_m$ value which defines the melting temperature ($T_m$) of hybrids, i.e. the temperature at which 50% of the double-stranded oligonucleotide strands are separated. Various formulas for calculating $T_m$ values are known to the person in the art. Conditions conducive for hybridizing in the context of the present invention may include the use of buffer containing reagents to maximize the formation of duplex and to inhibit non-specific binding of the detection molecule to its target sequence. If required, the final concentration of the respective detection molecules such as, for example, the particular peptide nucleic acids employed in the context of a particular experiment, may be optimized for each reaction. Conditions conducive for hybridization also include incubating the detection molecule with the target molecule for a sufficient period of time to allow optimal annealing. Preferably, hybridizing according to the present invention refer to hybridization conditions in which the detection molecule, such as the peptide nucleic acid, is incubated with its target molecule in solution, preferably by forming a hybridization mixture. The hybridization conditions according to the present invention are, e.g., illustrated in detail in the example section. Hybridization according to the present invention is preferably carried out by heating the sample to a temperature of between 70° C. to 80° C. and by subsequently cooling the sample to a temperature of 5 to 15° C. In particular case, hybridisation may also be performed at room temperature (i.e. about 25° C.). Moreover, it may advantageous to optimize the temperature conditions on a case to case basis, such as in view of and dependent on the pH. Such an optimization may easily be performed by any person skilled in the art.

The term "fluorescent moiety" as used herein generally refers to any substance or agent which can be attached and/or linked to the detection molecule of the invention, and which can be employed to visualize and/or to quantitate the oligonucleotide of interest after its hybridization to the target sequence by means of fluorescent readout. In the context of the present invention, the fluorescent moiety is preferably a fluorescent label or a fluorophore designed for high sensitive applications such as fluorescence microscopy, flow cytometry or in situ hybridization. Routinely used fluorescent labels include, but are not limited to, fluorescein dyes, rhodamine dyes, or cyanine dyes. Preferred fluorescent labels of the present invention include all sorts of Atto dyes, and preferably the fluorescent labels Atto 425, Atto 520, and Atto 610, or alike. The fluorescent label may also be selected from the group of fluorescein dyes such as carboxyfluorescein (FAM), 6-carboxy-4',5'-dichloro-2'7'-dimethoxyfluorescein (JOE), fluoresceinisothiocyanat (FITC), or 5'-Hexachloro-Fluorescein-CE Phosphoramidite (HEX); rhodamine dyes such as, e.g., carboxy-X-rhodamine (ROX), Texas Red and tetramethylrhodamine (TAMRA), cyanine dyes such as pyrylium cyanine dyes, DY548, QUASAR® 570, or dyes such as Cy3, Cy5, Alexa 568, or alike. The choice of the fluorescent label is typically determined by its spectral properties and by the availability of equipment for imaging. The use of fluorescent labels in quantitative assays is a standard procedure well known to the person skilled in the art, and fluorescent labels are commercially available from diverse suppliers including, for example, INVITROGEN® (USA).

In a preferred embodiment, the at least two detection molecules employed in the context of the present invention are each labelled with a fluorescent moiety of the same identity.

The use of identical fluorescent labels allows for the fluorescent readout using only one detection channel, i.e. the fluorescent readout can be carried out at only one wavelength. The use of only one fluorescent detection channel not only facilitates the whole experimental set up but also allows for a more simplified and reliable quantitative fluorescent readout. However, it is equally preferred in the context of the present invention that the identity of the fluorescent label in the context of the at least two detection molecules is different, i.e. that the detection molecules are labelled with fluorescent moieties of different identity.

The method of the present invention is in principle applicable for the detection of oligonucleotides of all kinds of length. The method as described herein, however, is particularly suitable for the multiplex detection of oligonucleotides of identical or similar length, including, for example, small regulatory RNA molecules, such as, for example microRNAs, therapeutic oligonucleotides such as siRNA, antisense oligonucleotides or decoy oligonucleotides.

In the context of the present invention, the terms "detection" or "detecting" generally mean visualizing, analyzing and/or quantifying the hybridized detection molecule-oligonucleotide moiety of interest. In particular, the term "detecting" refers to any method known in the art which is applicable to detect fluorescently labeled molecules by means of fluorescence readout.

The term "detection molecule-oligonucleotide moiety/moieties" as used herein refers to the complex composed of the fluorescently labeled detection molecule, preferably a peptide nucleic acid hybridized to its complementary oligonucleotide target sequence. A detection molecule-oligonucleotide moiety according to the present invention thus refers to a double stranded molecule, or a duplex structure. During anion-exchange chromatography, the double stranded molecules are separated from the free, non-hybridized detection molecules which elute in the void volume of the HPLC system. Separation and thus purification of detection molecule-oligonucleotide moieties according to the present invention is further exemplified by the examples of the present invention. In the context of the present invention, the detection molecule-oligonucleotide moiety/moieties preferably refer to duplexes composed of fluorescently labeled peptide nucleic acids and their respective oligonucleotide target sequences derived from the biological sample to be analysed.

The term "quantitative fluorescence readout" generally means all kind of imaging methods known in the art that are suitable to visualize, detect, analyze and/or quantify the oligonucleotides of interest from a sample when hybridized to its respective detection molecule. Quantitative fluorescence readout according to the present invention includes a quantitative comparison of the peak heights, the peak widths and/or the peak areas with either an internal standard as described herein or by comparison with an external standard in form of an external calibration curve. Quantitative fluorescent readout according to the present invention is, e.g., exemplified in FIGS. 8 to 13 of the examples.

The method of the present invention can further successfully be applied to detect more than two oligonucleotides of interest in parallel from one sample. That is, in a preferred embodiment, the method of the present invention is applied for detecting multiple oligonucleotides of equal length in parallel in one experimental set up, such as, for example three, four, five, six, seven, eight, nine or ten distinct oligonucleotides in parallel. In this context, the target oligonucleotides of interest may be either identical or similar in length, or both. That is, if several distinct target oligonucleotides of interest are detected in parallel by the method of the present invention, such as, for example, a total of seven distinct target oligonucleotides, four of these target oligonucleotides may have identical lengths while the remaining three oligonucleotides of interest may be of similar length, i.e. vary in lengths by one or more nucleotides, preferably by five nucleotides at the maximum.

Accordingly, in another preferred embodiment, the method of the invention is for quantitatively detecting three, four, five, six, seven, eight, nine or ten distinct oligonucleotides in parallel from one biological sample.

Preferably, at least two distinct oligonucleotides of equal length are either composed of DNA or RNA nucleotides. That is, the at least two distinct oligonucleotides to be detected are preferably DNA or RNA oligonucleotides.

More preferably, the at least two distinct oligonucleotides of equal length are selected from the group consisting of miRNAs (miRNAs), small interfering RNAs (siRNAs), short activating RNAs (saRNAs), decoy oligonucleotides, antisense oligonucleotides, aptamers, and spiegelmers.

The terms "miRNA" or "microRNA", which are equally used in the context of the present invention, generally refer to an RNA molecule of short length which is endogenously expressed within a cell. In particular, the term "miRNA" refers to a single-stranded RNA of about 20 to 25 nucleotides in length which is generated from an endogenous hairpin-shaped precursor molecule of approximately 70 nucleotides in length. Genes encoding miRNAs are found in the genomes of humans, animals, plants and viruses, respectively.

The term "small-interfering RNA" or "siRNAs" generally means an RNA molecule which is produced upon exogenous delivery of a dsRNA molecule into a cell, upon transgenic expression of long dsRNA, or which is introduced into a cell by gene transfer, cell transfection or cell transduction, or which is endogenously expressed in a cell. The term "siRNA" also means a short regulatory RNA molecule which is implicated in RNA interference and gene silencing, preferably resulting in the degradation of a target RNA transcript. A small-interfering RNA may be a single-stranded RNA or may be a double-stranded RNA consisting of two separate RNA strands, i.e. a sense and an antisense strand. Small-interfering RNAs are generally 18-30 nucleotides in length.

A "short activating RNA" or "saRNA" generally refer to any kind of double-stranded RNA (dsRNA) molecule which is capable of targeting sequences in gene promotors, thereby inducing target gene expression in a phenomenon also referred to as dsRNA-induced transcriptional activation. That is, saRNAs are known to the skilled person as small dsRNAs which induce transcriptional activation in human cells by targeting promotor regions (see, e.g., Li et al., 2006, Proc Natl Acad Sci USA 103: 17337-17342; Janowski et al., 2007, Nat Chem Biol 3: 166-173).

The term "decoy oligonucleotide" generally refers to any kind of antisense agent which allows for the specific inhibition of transcription factor function in living cells. Preferably, decoy oligonucleotides are short synthetic fragments of DNA or RNA resembling and/or mimicking complementary sequences of nucleic acids or proteins (such as, for example, transcription factors), thereby preventing transcription factors from binding to target gene promotor regions.

The term "antisense oligonucleotide" as used herein means any kind of DNA or RNA oligonucleotide with a sequence complementary to the sequence of a specific mRNA molecule of interest. Upon hybridization to its target sequence, the antisense oligonucleotides can specifically inhibit expression of the mRNA target with the consequence of inducing a blockade in the transfer of genetic information from DNA to protein. An antisense oligonucleotide according to the present invention also refers to any oligonucleotide which inhibits gene expression via annealing to a target sequence, thereby activating enzymatic cleavage by RNAse H. Antisense oligonucleotides are well known in the art as therapeutic agents or as tools to study gene function (for review, see, e.g., Dias and Stein, 2002, Molecular Cancer Therapeutics Vol. 1, 347-355).

In the context of the present invention, an "aptamer" generally refers to all sorts of oligonucleotide molecules that bind to a specific target molecule. Aptamers are usually created by selection from a large random sequence pool, but natural aptamers also exist. The term "aptamer" as used herein also includes nucleic acid aptamers that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

A "spiegelmer" generally means an L-ribonucleic acid aptamer or an L-RNA aptamer. Spiegelmers are RNA-like molecule built from L-ribose units. Spiegelmers are artificial oligonucleotides named for being a mirror image of natural oligonucleotides. Spiegelmers, or alternatively, L-RNA aptamers are a particular form of aptamers. Due to their L-nucleotides, they are highly resistant to degradation by nucleases. Spiegelmers are considered potential therapeutic drugs which are routinely tested in clinical trials.

As already described, the different surface charge(s) of the detection molecules employed in the context of the present invention have to be designed as such that, upon annealing to their target sequences, they are able to alter the binding affinity of the respective target oligonucleotides of equal length in the context of anion-exchange high performance liquid chromatography (AEX-HPLC), in particular when applied to a chromatography column and subsequently separated by elution from the column. The number of additional chemical modification(s) in the detection molecule suitable or necessary for shifting the target oligonucleotide's overall surface charge to either a more positive or negatively charged range of surface charges may be decided on a case to case basis dependent on the target molecules of interest to be detected. In general, the at least two detection molecules employed in the context of the present invention may comprise several and different surface charge(s) to all sorts of degree, including additional neutral, additional positive, additional negative, multiple additional positive and/or multiple additional negative charges.

That is, the detection molecules of the invention, preferably the peptide nucleic acids, may differ from each other by either one, two, three, four, five, six, seven, eight, nine, ten, eleven, twelve or more positive surface charge(s), or by either one, two, three, four, five, six, seven, eight, nine, ten, eleven, twelve or more negative surface charge(s), or by any combination of these alternatives. Combinations of different surface charges employed in the context of the present invention to successfully separate target oligonucleotides of equal length are further described in the example section of the present invention, in particular in FIGS. 3, 5, and 10 to 13, including Tables 3 and 5.

Accordingly, in a preferred embodiment, the different surface charges of the at least two detection molecules are selected from the group of neutral, negative and positive charges, preferably selected from a combination of neutral and negative, neutral and positive, and/or negative and positive charges, more preferably selected from multiple negative charges, multiple positive charges, or any combination thereof.

That is, in one preferred embodiment, the different surface charges of the at least two detection molecules, preferably of the at least two peptide nucleic acids, are selected from the group of neutral, six additional negative charges and five additional positive charges. Separation of at least two distinct oligonucleotides in parallel from one sample using anion-exchange high performance liquid chromatography (AEX-HPLC) and detection molecules with this selection of surface charges is, for example, exemplified in FIG. 3, FIG. 5 and Table 3.

Equally preferred is that the different surface charges of the at least two detection molecules, preferably of the at least two peptide nucleic acids, are selected from the group of neutral, four additional negative charges and eight additional negative charges. Separation of at least two distinct oligonucleotides in parallel using anion-exchange high performance liquid chromatography (AEX-HPLC) and detection molecules with this selection of surface charges is, for example, exemplified in FIG. 11, FIG. 12, FIG. 13, and Table 5.

Equally preferred is any combination of different surface charge(s) as outlined above. That is, any combination of detection molecules with different surface charges which provide for a sufficient and desirably high separation by anion-exchange chromatography during the elution of particular target molecules is envisioned and may be applied in the context of this invention, including the combination of neutral with multiple negative and/or multiple positive surface charges, or the combination of multiple negative charges with multiple positive surface charges, or any combination of multiple positive charges or, alternatively, of multiple negative surface charges alone.

The term "multiple charges" as used herein generally means the presence of two, three, four, five, six, seven or eight additional negative and/or positive charges, i.e. a difference in net charge in form of two, three, four, five, six, seven or eight negative and/or positive charges. Preferably, "multiple charges" according to the present invention may also include a higher difference in net charge of the respective detection molecules, such as, for example nine, ten, eleven, or twelve additional positive and/or negative charges.

It is evident for the skilled person that the different surface charges of the detection molecules employed in the context of the present invention have to be designed as such that separation of the oligonucleotides of interest by anion-exchange chromatography can be carried out at sufficiently high resolution, i.e. that the binding affinities of the respective target molecules, in complex with their respective complementary detection molecules, are altered as such in that the target sequences distinctively separate from each other in the elution profile. That is, it is envisaged that the detection molecules, in particular the peptide nucleic acids of the present invention may comprise all sorts of different combinations of chemical modifications which are suitable to alter the molecule's surface overall charge accordingly. That is, the at least two detection molecules, preferably the at least two peptide nucleic acids of the present invention may comprise neutral charges in combination with several positive charges and/or several negative charges. Every combination of chemical combination with is suitable to provide a biochemical separation profile of high resolution is envisaged and may be applied in the context of the present invention. The chromatographic separation of oligonucleotides of equal length by anion-exchange chromatography at high resolution by the use of peptide nucleic acids with either neutral, positive and negative overall surface charge, is, for example, described in detail in the example section, in particular in FIGS. 10 to 13.

In a preferred embodiment, the negative surface charge(s) is/are characterized by the presence of at least two incorporated negatively charged amino acid residues or aminoglycine backbone modifications, preferably wherein the negatively charged amino acid residues are in form of glutamic acids.

In another preferred embodiment, the positive surface charge(s) is/are characterized by the presence of at least two incorporated positively charged amino acid residue or aminoglycine backbone modifications, preferably wherein the positively charged amino acid residue is in form of lysine.

Glutamic acid and lysine are preferred examples of charged amino acids which may be used as chemical modification to incorporate one or more additional positive or negative charge(s) into the peptide nucleic acids, respectively. Other amino acids which may change the detection molecule's, in particular the peptide nucleic acid's overall surface charge are equally preferred. Amino acids of different charges are well known in the art and common knowledge to the skilled person.

Equally preferred is that the additional positive and/or negative charges are incorporated into the detection molecule's backbone, in particular into the peptide nucleic acid's backbone via one or more aminoglycine backbone modification(s), preferably via the gamma position of the aminoglycine unit.

In a preferred embodiment, the amino acid modifications may be combined with modifications of the aminoglycine backbone.

That is, in a preferred embodiment, the at least two detection molecules, preferably the at least two peptide nucleic acids comprise either chemical modifications in form of additionally charged amino acids (positively or negatively charged, or both), chemical modifications in form of additional charged groups linked to the aminoglycine backbone, preferably via the gamma position (positively or negatively charged, or both), or any combination thereof. In this embodiment, the net charge of the peptide nucleic acid is the important criteria upon which the degree of chemical modification is decided. Examples of modified peptide nucleic acids according to the present invention are further exemplified in the examples.

In the context of the present invention, the term "forming a hybridisation mixture" generally means the provision of conditions under which the fluorescently labelled detection molecule of the invention can hybridize to its target oligonucleotide sequence, i.e. conditions under which the detection molecule can bind to its target sequence. The hybridization between the at least two detection molecules and their at least two distinct oligonucleotide target sequences includes the formation of complementary base pairs as defined by hydrogen bonding and hydrophobic interactions in equilibrium. That is, annealing and separation of the two complementary strands depend on a variety of factors, including temperature, salt concentrations, pH, the nature of probes and target molecules, and the composition of the hybridization solution. Conditions conducive to a successful hybridization according to the present invention also include the use of hybridization buffer containing reagents to maximize the formation of duplex and to inhibit non-specific binding of the respective detection molecule to non-target sequences.

In the context of the present invention, it has also found that forming a hybridization mixture under partial denaturing conditions may be advantageous in that degradation of the hybridized moieties is significantly reduced. Accordingly, in a preferred embodiment, the hybridization mixture is formed under denaturing conditions. In particular, hybridization under denaturing conditions according to the present invention may be carried out in the presence of denaturing agents, including, but not limited to, urea, formalin, dimethylformamide (DMF), N-Methyl-2-pyrrolidone (NMP), dimethylsulfoxide (DMSO), and guanidinium thiocyanate. Hybridization under partial denaturing conditions is further exemplified by the examples, including FIG. 5.

Accordingly, in a preferred embodiment, the hybridization mixture is formed in the presence of urea at a concentration of from 1 M to 5 M, more preferably in the presence of urea at a concentration of from 2 M to 4.5 M.

In the context of the present invention, is has further been found that anion exchange chromatography at an increased temperature results in improved separation profiles. Elution of the hybridized moieties at high temperatures is enabled due to the improved stability of the peptide nucleic acid-target duplex(es). Elution of hybridized peptide nucleic acid-oligonucleotide moieties at increased temperatures according to the present invention is further exemplified in the example section.

Hence, in the context of the present invention, the anion exchange high performance liquid chromatography (AEX-HPLC) in step c) is preferably performed at a temperature of from 30° C. to 75° C., preferably at a temperature of from 40° C. to 55° C., more preferably at a temperature of 50° C.

Furthermore, detection of the hybridized detection molecule-oligonucleotide moieties is carried out by quantitative fluorescent readout. Quantitative fluorescent readout according to the present invention involves the use of either internal or external standards. Quantitative fluorescent readout by the use of internal standards has been described in the context of the present invention. Alternatively, and equally preferred is that the quantitative fluorescent readout involves the use of external standards in form of a comparison to external calibration curves.

Accordingly, in a preferred embodiment, the quantitative fluorescent readout of step d) is characterized by comparing the fluorescent signals of the hybridized detection molecule-oligonucleotide moieties to internal standard or to an external standard in form of an external calibration curve.

Preferably, the external calibration curve is derived from a dilution series of target molecules of known concentration(s) or of know molar weight(s) which are treated under identical conditions as the samples of interest, in particular by hybridizing the target molecules with a fluorescently labelled detection molecule.

In this context, the fluorescently labelled detection molecule is preferably selected from the group consisting of fluorescently labelled peptide nucleic acids, phosphorodiamidate morpholine oligomers (PMOs) and ugimers.

Moreover, the external calibration curve according to the present invention is preferably generated by series dilutions of at least three, preferably five different concentrations of a mixture comprising the target molecule and its respective fluorescently labelled detection molecule at equimolar concentrations. Quantitative fluorescent readout by the comparison of fluorescent signals to an external calibration curve is exemplified by the examples of the present invention such as, for example, in FIG. 9.

In this context, the fluorescently labelled detection molecule is generally synthesized to match to a nucleotide sequence of interest and can be used to detect, analyse, and/or visualize said nucleotide sequence on a molecular level. It will be evident to the skilled person that the detection molecule of the present invention has a length suitable to provide the required specificity for annealing with its target molecule. The detection molecule is preferably composed of at least 10 nucleotides, more preferably of at least 15 nucleotides, and preferably comprises at least one fluorescent moiety in form of a fluorescent label.

In a further aspect, the present invention relates to a kit, comprising (i) at least two detection molecules complementary to at least two distinct oligonucleotides of equal length of interest, wherein each of the detection molecule is labelled with at least one fluorescent moiety, and wherein the detection molecules are characterized by different surface charges; and (ii) a hybridization mixture, wherein the hybridization mixture preferably contains proteinase K and a proteinase K digestion buffer.

The detection molecules of the kit are preferably selected from the group consisting of peptide nucleic acids (PNAs), phosphorodiamidate morpholino oligomers (PMOs) and ugimers. More preferably, the detection molecules of the kit are in form of peptide nucleic acids.

The term "hybridisation mixture" as used herein generally refers to any kind of aqueous solution, buffer or liquid which allows for the suspension of biological samples, including preferably the suspension of the provided detection molecules and/or any additional fluorescently labelled molecules. The hybridisation mixture provides suitable aqueous conditions for hybridizing the detection molecules to their respective target sequences and may, therefore, contain any kind of salt(s) or buffer systems at a particular pH value, such as, for example, pH 7 or 8.

It is obvious to a person skilled in the art that the kit of the present invention may further comprise a variety of standard components such as, for example, buffers and/or reagents to stop a particular reaction. The skilled person will be able to adjust the components of the kit to the prevailing intended use which depends, e.g., on the detection system, the cells and/or tissues examined, the target sequence of the oligonucleotides to be detected, the fluorescent label(s) etc.

Preferably, the kit of the present invention comprises at least two detection molecules which are each labelled with at least one fluorescent moiety, wherein the fluorescent moiety has the same identity.

Accordingly, in a preferred embodiment, the at least two detection molecules of the kit are each labelled with the same fluorescent moiety, preferably selected from the group consisting of, but not limited to, Atto 425, Atto 520 and Atto 610. The use of identical fluorescent moieties has the advantage that the quantitative fluorescent readout can be carried out at only one wavelength which not only facilitates the experimental set up but also provides an improved basis for quantitative comparison and fluorescent readout.

Equally preferred, however, is that the at least two detection molecules are each labelled with at least two fluorescent moieties of the same identity. It is further envisaged in the context of the present invention that the at least two detection molecules are each labelled with more than two fluorescent moieties of the same identity, such as, for example, with at least three, four, five or six fluorescent moieties of the same identity.

Alternatively, the kit of the present invention may comprise at least two distinct detection molecules complementary to at least two distinct oligonucleotides of equal length of interest, wherein the detection molecules are each labelled with at least one fluorescent moiety of different identity, such as, for example, Atto 425 and Atto 610, Atto 425 and Atto 520, or, alternatively, Atto 520 and 610. It is to be understood by the skilled person that the choice of the identity of the different fluorescent labels will depend on the individual experimental set up.

In another preferred embodiment, the at least two detection molecules are each labelled with at least one fluorescent moiety, more preferably with at least two fluorescent moieties, of different identity.

Equally preferred is that the kit comprises several different fluorescently labeled detection molecules in case multiple detection of a variety of distinct target oligonucleotides is envisaged. That is, in a preferred embodiment, the kit may comprise three, four, five, six, seven, eight, nine or ten different detection molecules for the parallel quantitative detection of at least three, four, five, six, seven, eight, nine or ten distinct oligonucleotides of equal length. Equally preferred is that the kit may comprise even more than 10 different detection molecules for the parallel quantitative detection of even more than 10 different target oligonucleotides. It is evident for the skilled person that is this context, the fluorescent label(s) are chosen to best experimental practice, i.e. the fluorescent labels may be either identical or different, or both, whatever may be suitable for an optimal chromatographic resolution and the separation of a particular selection of distinct targets of interest.

In another preferred embodiment, the kit further comprises at least one fluorescently labelled molecule complementary to a binding site of the at least two detection molecules, wherein this binding site is not involved in target sequence binding.

That is, in the context of this preferred embodiment, the at least two detection molecules are designed as such to encompass at least one additional binding site for the at least one fluorescently labelled molecule, wherein this binding site is not complementary to any target sequence of interest. Accordingly, the at least two detection molecules preferably contain a binding site which is not involved in target sequence binding.

Further in this embodiment, the at least two detection molecules are preferably labeled with the same fluorescent moiety as the fluorescently labelled molecule.

The term "fluorescently labeled molecule" as used herein generally means any kind of molecule with neutral surface charge which may be able to anneal to a particular, ubiquitous binding site of the detection molecules used in the particular assay. Annealing of an additional fluorescently labeled molecule aims at multiplying the fluorescent signal generated by the respective detection molecules. In this context, the fluorescently labeled molecule is preferably selected from the group consisting of, but not limited to, peptide nucleic acids, phosphorodiamidate morpholino oligomers (PMOs) and ugimers.

By the use of one or more additional fluorescently labelled molecule(s), the sensitivity of the method described herein may be significantly increased. The use of one or more additional fluorescently labelled molecule(s) is particularly suitable for detecting oligonucleotides of interest of low abundance. Preferably, the additional fluorescently labelled molecule(s) is/are designed as such that binding takes place at a particular binding site of the respective detection molecule, preferably of the respective peptide nucleic acid(s), which is not involved in binding of the particular oligonucleotide target sequence of interest. This binding site may be in form of a stretch of nucleotides which is designed in a way to enable the annealing and/or the hybridization of the complementary additional fluorescently labelled molecule(s). In the context of the present invention, the binding site may be composed of about 10 to 20 nucleotides or more, and may reveal any sequence which is considered appropriate for establishing complementary base pairing to an oligonucleotide molecule of interest. The binding site does preferably not refer to the sequence of the oligonucleotides to be detected. Sequences of universal primer binding sites such as palindrome sequences are well known to the person skilled in the art, and can, e.g., be obtained from public databases including the NCBI gene bank (National Center for Biotechnology Information, Maryland, USA).

In principle, the use of such a fluorescently labelled molecule for increasing the sensitivity of the fluorescent readout generated by the use of the detection molecules as defined herein is also applicable and envisaged in the context of the method of the present invention. Hence, in a preferred embodiment, the method of the present invention further comprises the step of adding a fluorescently labelled molecule to the biological sample or to the hybridization mixture, wherein the fluorescently labelled molecule is complementary to a binding site of the at least two detection molecules which is not involved in target binding. In this embodiment, the least two detection molecules are preferably labeled with the same fluorescent moiety as the fluorescently labelled molecule.

In a further aspect, the present invention relates to the use of at least two detection molecules as defined in the context of the present invention for quantitatively detecting at least two distinct oligonucleotides of equal length in parallel from one biological sample, wherein the detection is preferably carried out as defined by any of the embodiments described herein.

The use of at least two detection molecules as defined in the context of the present invention for quantitatively detecting at least two distinct oligonucleotides of equal length in parallel from one biological sample is particularly suitable in the context of diagnostic purposes, such as, for example, for the diagnosis of a particular disease which goes along with an increase or a decrease of one or more particular target sequence(s) which, in turn, may represent a biomarker for the diagnosis of a particular disease.

Hence, in a preferred embodiment, the use of the at least two distinct detection molecules as defined herein is for diagnostic purposes, in particular for diagnosing a disease, more in particular for diagnosing renal diseases such as, for example, acute kidney injury.

Figure 13:
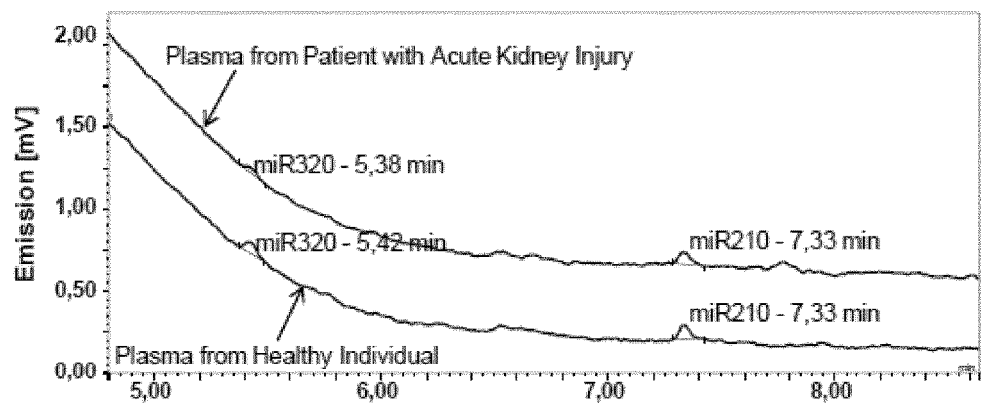

The use of at least two distinct oligonucleotide for quantitative detection of at least two oligonucleotide target sequences of interest in the context of diagnostic purposes, in particular the quantitative detection of particular target sequences as biomarkers for acute kidney injury, is, for example, exemplified in FIG. 13.

The following Figures and Examples are intended to illustrate various embodiments of the present invention. As such, the specific modifications discussed therein are not to be understood as limitations of the scope of the invention. It will be apparent to the person skilled in the art that various equivalents, changes, and modifications may be made without departing from the scope of the invention, and it is thus to be understood that such equivalent embodiments are to be included herein.

FIGURES

FIG. 1 A. Graphical representation of a gamma modification with lysine on a peptide nucleic acid backbone. FIG. 1 B. Graphical representation of the fluorescence dye Atto425 coupled to cysteine via the maleimide ring structure. FIG. 1 C. Graphical representation of the fluorescence dye Atto425 coupled via NHS-ester and the chemical structure of the O-linker.

Figure 2:
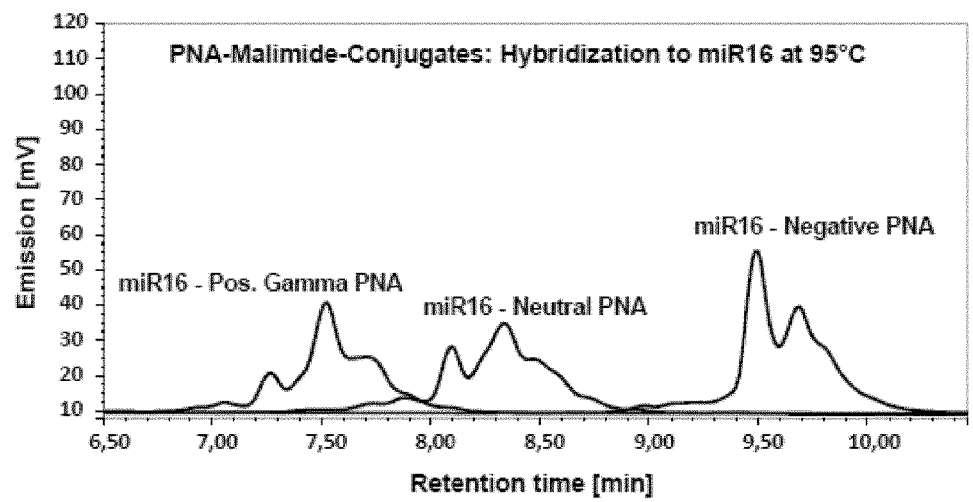

FIG. 2. Influence on the retention times by the peptide nucleic acids' surface charges. Chromatographic experimental setup: HPLC system 1, DNAPAC®-100-column with a column temperature of 50° C., buffer pH 8 with a gradient of 5-55% buffer B in 9 minutes.

Figure 3:
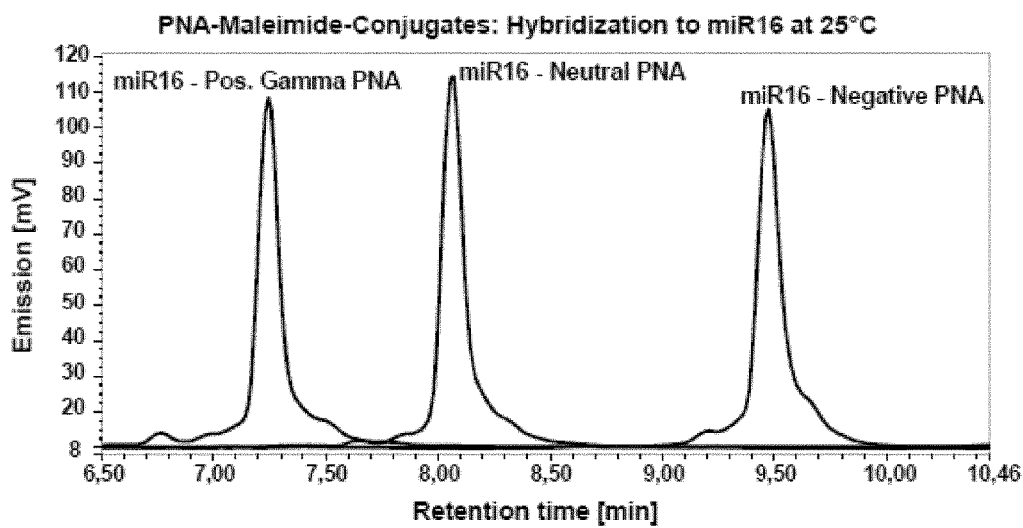

FIG. 3. Comparison of chromatograms derived from the three duplexes miR16-pos. gamma, miR16-Neutral and miR16-negative. Hybridisation temperature of 0° C. after heating to 95° C. and room temperature (RT), respectively. Chromatographic experimental setup: HPLC system 1, DNAPAC®-100-column with a column temperature of 50° C., buffer pH 8 with a gradient of 5-55% buffer B in 9 minutes.

Figure 4:
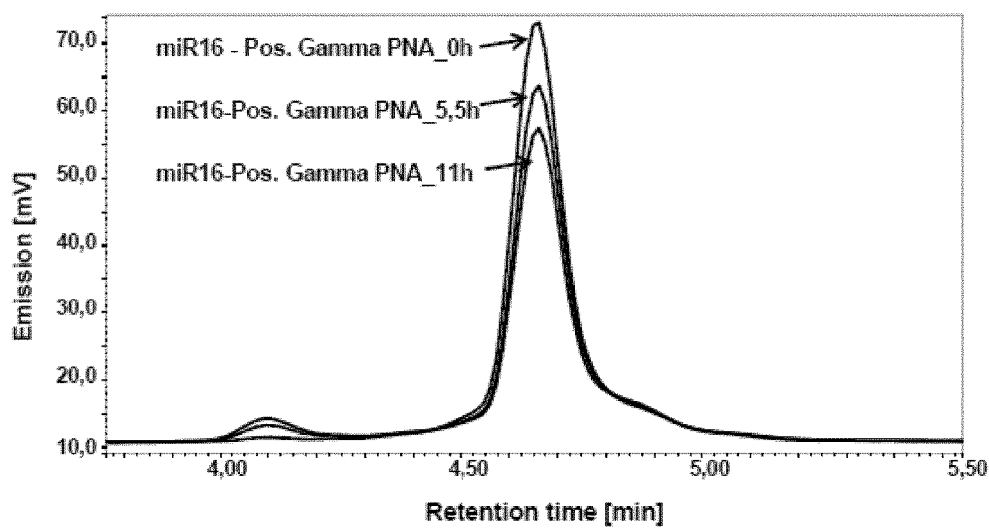

FIG. 4. Comparison of chromatograms of miR16-pos. gamma after 0h, 5.5 hrs and 11 hrs of incubation time. Chromatographic experimental setup: HPLC system 1, DNAPAC®-100-column with a column temperature of 50° C., buffer pH 8 with a gradient of 5-55% buffer B in 7 minutes and hybridization at 25° C. without urea.

Figure 5:
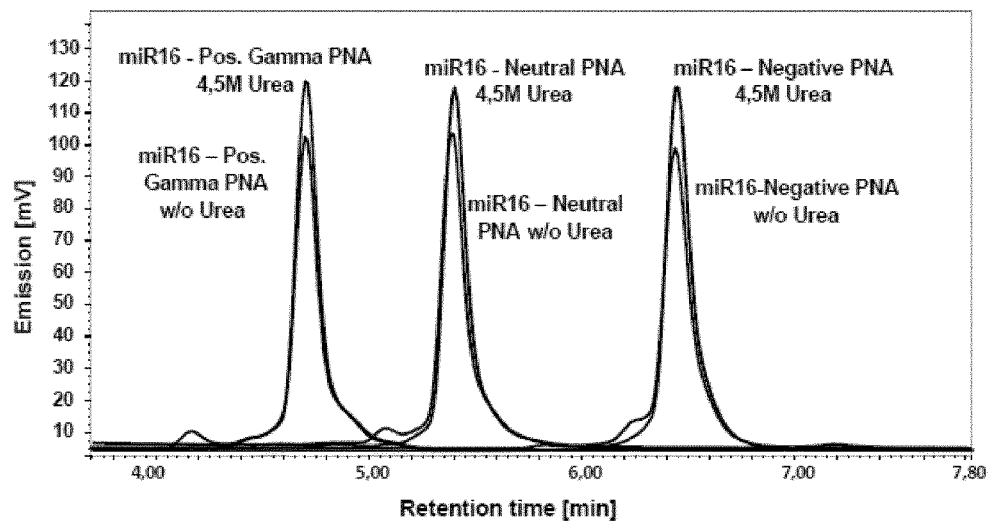

FIG. 5. Comparison of hybridization set ups with and without 4.5 M urea using miR16-pos. gamma, miR16-Neutral and miR16-negative. Chromatographic experimental setup: HPLC system 1, DNAPAC®-100-column with a column temperature of 50° C., buffer pH 8 with a gradient of 15-66% buffer B in 7 minutes.

Figure 6:
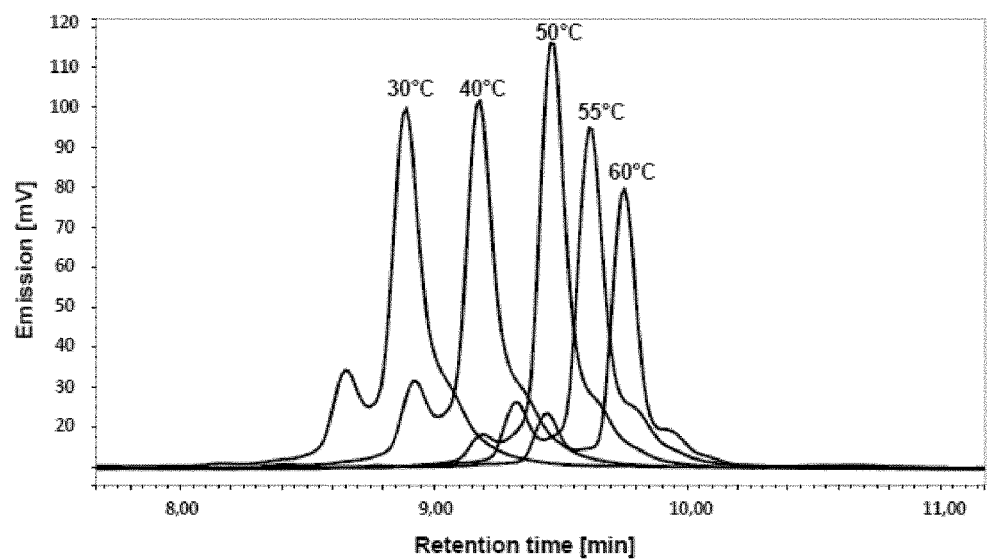

FIG. 6. Comparison of chromatography profiles at different column temperatures using miR-16 negative. Chromatography was performed at a column temperature of 30° C., 40° C., 50° C., 55° C. and 60° C., respectively. Chromatographic experimental setup: HPLC system 1, DNAPAC®-100-column, buffer pH 8 with a gradient of 5-55% buffer B in 9 minutes and hybridization at 40° C.

Figure 7:
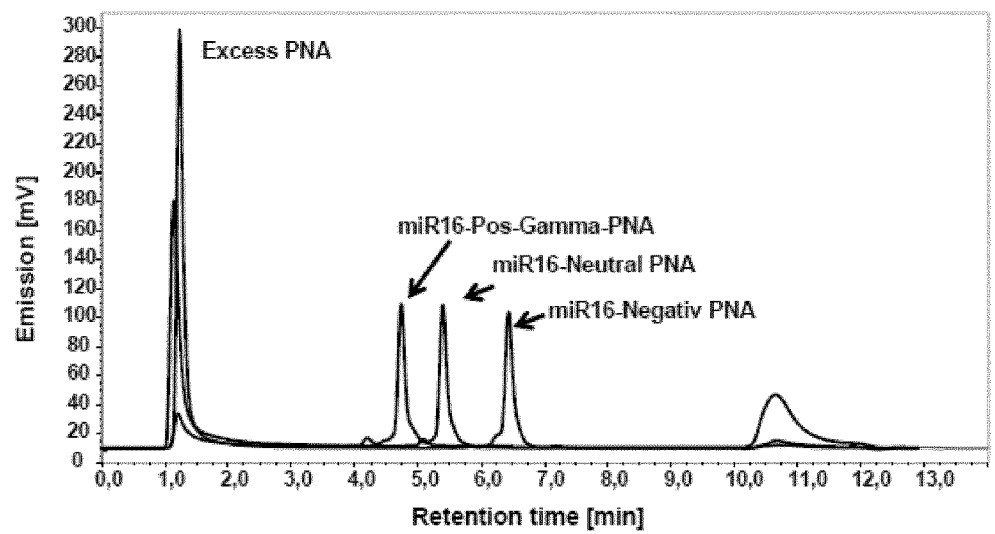

FIG. 7. Chromatograms of miR-16-pos. gamma, miR16-neutral and miR16-negative. Chromatographic experimental setup: HPLC system 1, DNAPAC®-100-column with a column temperature of 50° C., buffer pH 8 with a gradient of 15-66% buffer B in 7 minutes and hybridization at 25° C.

Figure 8:
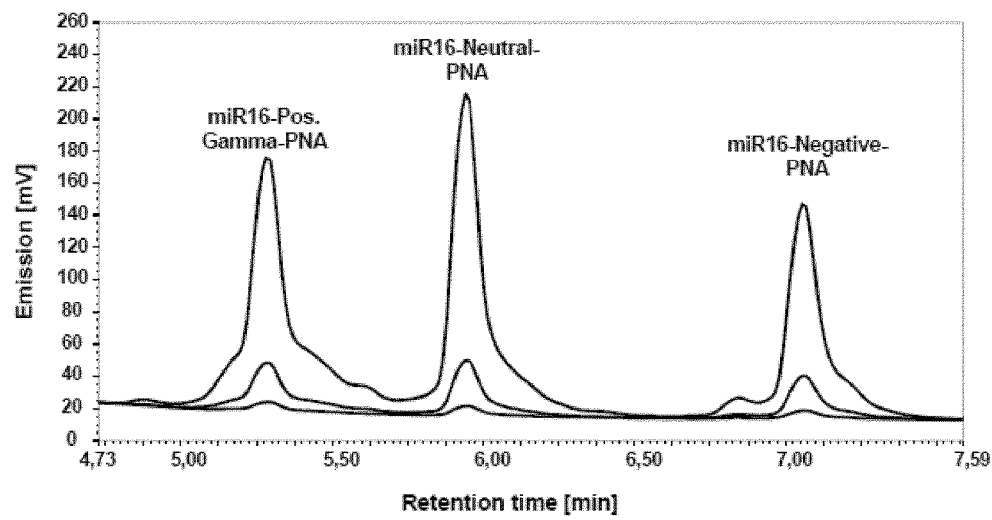

FIG. 8. Chromatograms of a 1:1:1 calibration sample mixture with miR-16-positive gamma, miR16-neutral and miR16-negative. Chromatographic experimental setup: HPLC system 1, DNAPAC®-100-column with a column temperature of 50° C., buffer pH 8 with a gradient of 15-66% buffer B in 7 minutes and hybridization at 25° C. in the presence of 4.5 M urea.

Figure 9:
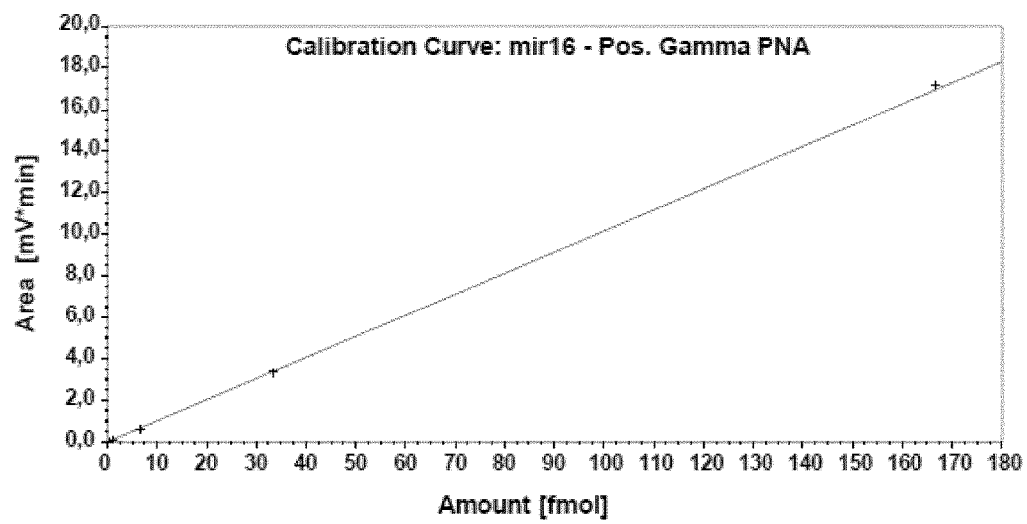
Figure 9:
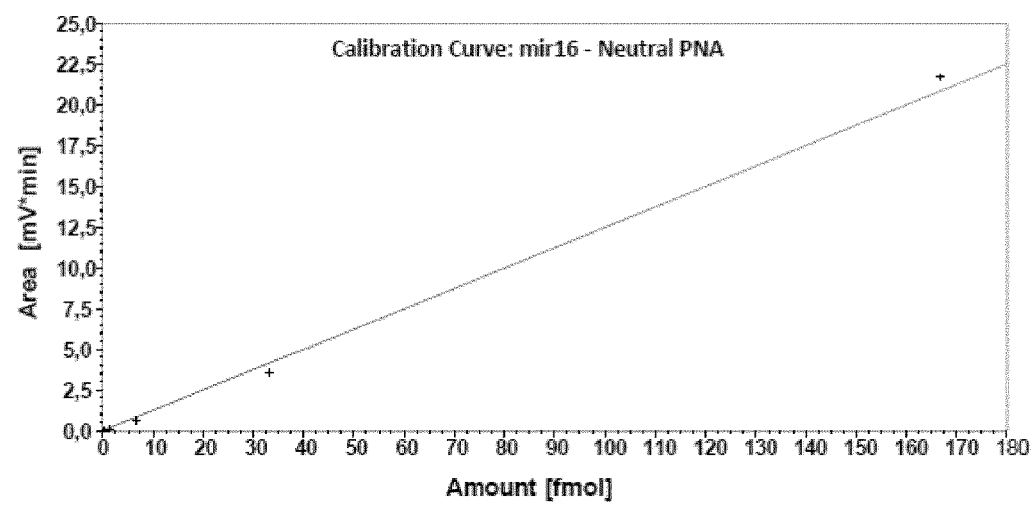
Figure 9:
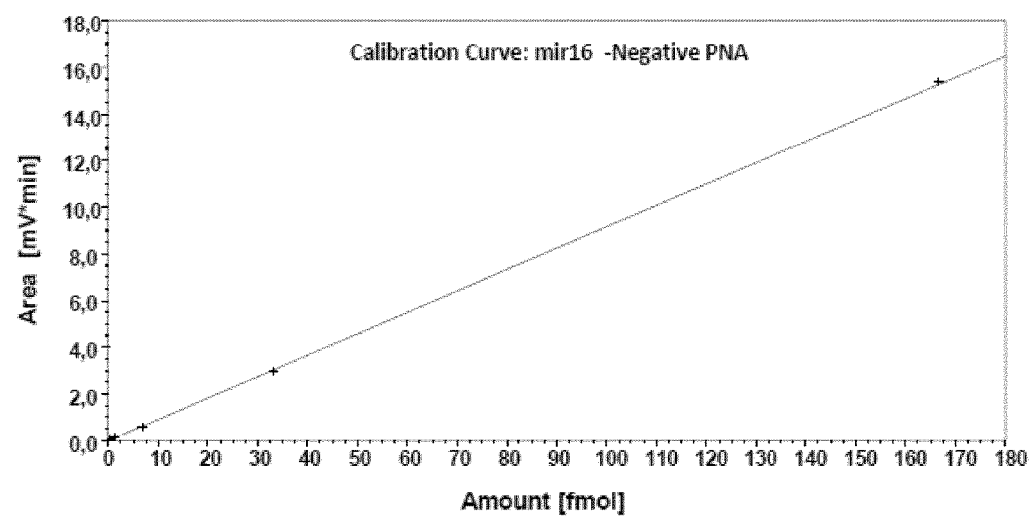

FIG. 9 A. Calibration curve of miR-16-positive gamma. FIG. 9 B. Calibration curve of miR-16-neutral. FIG. 9 C. Calibration curve of miR-16-negative. Chromatographic experimental setup in FIGS. 9 A, 9 B and 9 C, respectively: HPLC system 1, DNAPAC®-100-column with a column temperature of 50° C., buffer pH 8 with a gradient of 15-66% buffer B in 7 minutes and hybridization at 25° C. in the presence of 4.5 M urea.

Figure 10:
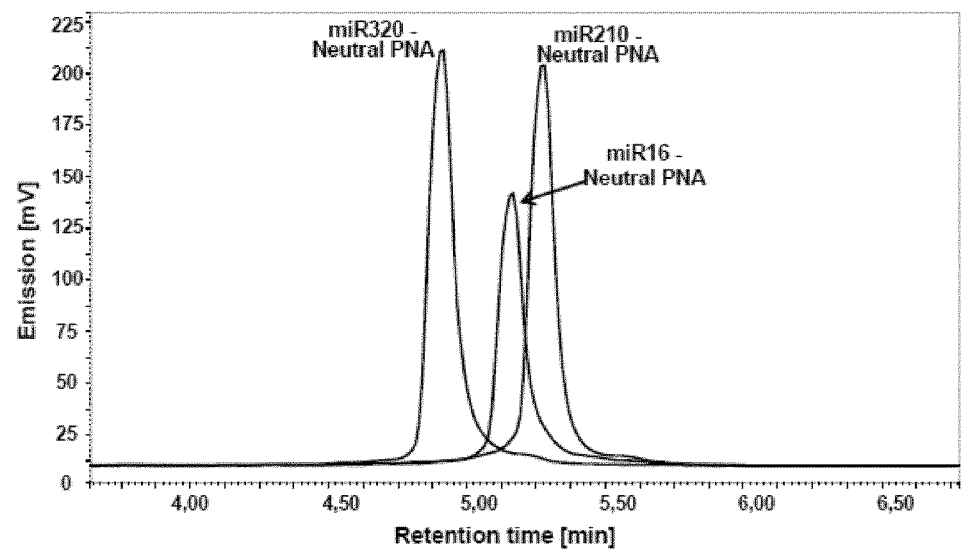

FIG. 10. Chromatograms of miR-16-neutral, miR210-neutral and miR320-neutral derived from three independent measurements. Chromatographic experimental setup: HPLC system 2, DNAPAC®-100-column with a column temperature of 50° C., buffer pH 8 with a gradient of 15-66% buffer B in 7 minutes and hybridization at 25° C. in the presence of 4.5 M urea.

Figure 11:
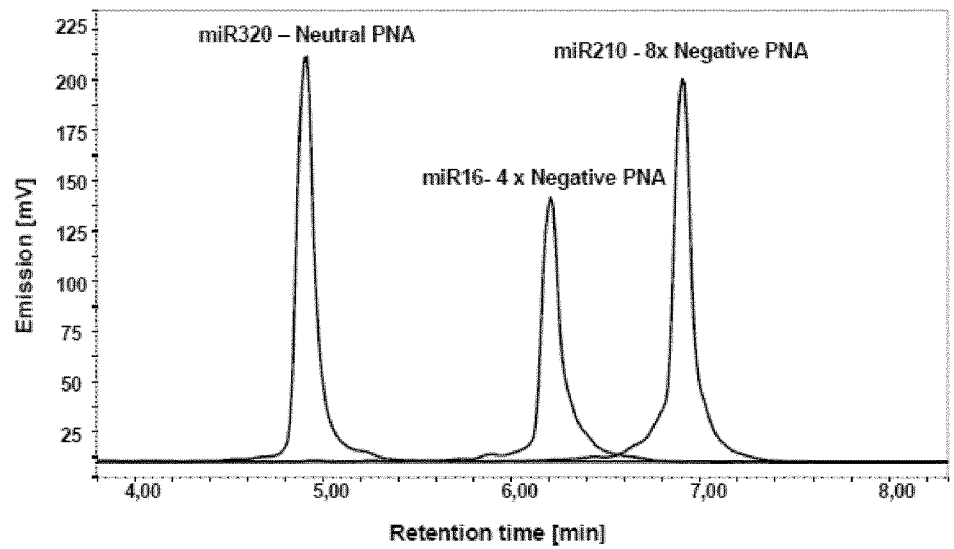

FIG. 11. Chromatograms of miR320-neutral, miR16-4× negative and miR210-8× negative. Chromatographic experimental setup: HPLC system 2, DNAPAC®-100-column with a column temperature of 50° C., buffer pH 8 with a gradient of 15-66% buffer B in 7 minutes and hybridization at 25° C. in the presence of 4.5 M urea.

Figure 12:
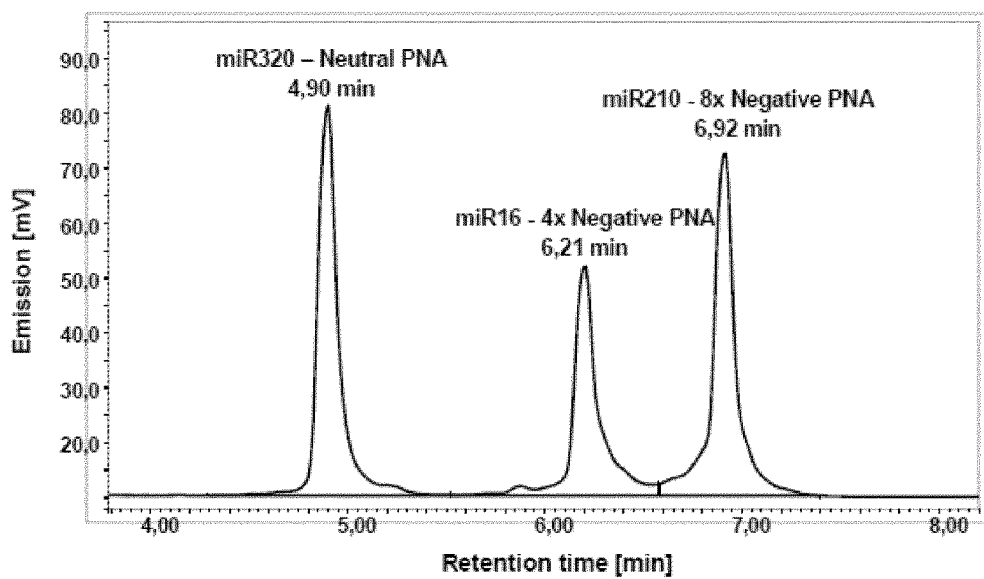

FIG. 12. Separation of miR320-neutral, miR16-4× negative and miR210-8× negative in one experiment via HPLC. Chromatographic experimental setup: HPLC system 2, DNAPAC®-100-column with a column temperature of 50° C., buffer pH 8 with a gradient of 15-66% buffer B in 7 minutes and hybridization at 25° C. in the presence of 4.5 M urea.

FIG. 13. Comparison of HPLC chromatograms derived from plasma of subject CTL8 of the control group and from plasma of subject AKT154 with acute kidney injury. Chromatographic experimental setup: HPLC system 2 with sensitivity of the detection level at middle 16×, DNAPAC®-100-column with a column temperature of 50° C., buffer pH 8 with a gradient of 20-60% buffer B in 7 minutes and hybridization at 80° C.

EXAMPLES

MicroRNAs (miRNAs) are short single stranded non-coding RNAs containing about 22 nucleotides. They have regulatory function with profound impact on many biological processes in development, differentiation, proliferation and apoptosis. They show a high potential in diagnosis and treatment of many diseases. In this work the ratio between three distinct miRNAs, namely miR16, miR210 and miR320 involved in acute kidney injury (AKI), was evaluated. The assay developed by Roehl et al. (WO 2010/043512 A1) was improved to allow the simultaneous detection of the three miRNAs from a biological matrix. A sample preparation without extraction, purification and amplification steps was used. The sample preparation is based on an initial cell lysis with proteinase K. For the measurement by AEX-HPLC the samples were hybridized with the complementary peptide nucleic acids (PNAs). PNAs represent modified DNA strands whose sugar phosphate backbones, which are negatively charged, are replaced by the electroneutral N-(2-Aminoethyl) glycine backbone. The PNAs were modified with negative or positive charges to allow miRNAs separation in one AEX-HPLC measurement. The hybridization of PNA and miRNA is followed by the simultaneous quantitative detection of the three miRNAs in human plasma by AEX-HPLC technique and fluorescence detection. The results showed that miR210 and miR320 may be used as biomarker for acute kidney injury as the ratio of miR210 and miR320 changes in the case of AKI. Consequently, these miRNAs could be used as biomarker in the diagnosis of acute kidney injury.

In 2011, Roehl et al. developed a simplified method for the detection of oligonucleotides. This method allowed for the separation of single metabolites via HPLC (High Performance Liquid Chromatography) using a simplified and quick sample preparation without extraction, amplification or purification steps. In this assay, a proteinase K digestion was performed in the presence of an SDS (sodiumdodecylsulphate-containing buffer) to avoid the degradation of oligonucleotides in biological samples. The SDS, which interferes with the AEX (anion exchange chromatography) HPLC column, is precipitated in the presence of saturated potassium chloride solution. Subsequently, hybridization of the oligonucleotide of interest to a complementary fluorescently labelled PNA was carried out. The formed duplexes are detected by AEX-HPLC and fluorescence detection.

Presently, the parallel detection of different oligonucleotides of similar length via HPLC is only possible by using peptide nucleic acid molecules with various fluorescent dyes. Since these reveal different response factors (sensitivity of the detection), it is thereby not possible to rely on a direct comparison of the peak areas for analysing the molar ratios in that sample. The modification of PNAs, such as, for example, the introduction of surface charges either at the end(s) of the strand or within the sequence, provides the possibility to solve this problem and to detect several components in parallel by using only one fluorescent dye.

1. PNA-DESIGN

The peptide nucleic acid (PNA) can be modified by several techniques. On the one hand, surface charges can be introduced at either end of the sequence, respectively, in that the strand is modified with amino acids, such as, for example, lysin or glutamic acid. These amino acids have charged side chains at a particular pH value. On the other hand, positive charges can be generated within the sequence, for example by gamma modification with lysin (see FIG. 1A).

For being able to use a highly sensitive fluorescence detector, the peptide nucleic acid (PNA) is modified with a fluorescence dye, such as, for example, Atto425 at both ends of the sequence. For this, thiol-reactive Atto425 can be used which is coupled to the terminal cysteins using maleimid chemistry and via the thiol group to the rest of the sequence (see FIG. 1B).

Alternatively, amino-reactive Atto425 can be used. Here, the fluorescent dye is linked by employing NHS ester chemistry (N-hydroxysuccinimid ester) via the amino group of lysin or via the O linker with the rest of the chain (see FIG. 10).

Peptide nucleic acids form duplexes with complementary DNA or RNA having high specificity and selectivity via Watson-Crick base pairs. The thereby formed PNA-DNA and PNA-RNA hybrids reveal a high stability, since electrostatic repulsion between PNA and DNA/RNA is avoided due to the neutral backbone of the PNA (Egholm et al. (1993) Nature, 365: 566-568). Moreover, the peptide nucleic acid shows high stability against enzymes such as nucleases, proteases and peptidases (Demidov et al. (1994) Biochemical Pharmacology, 48: 1310-1313).

2. OBJECTIVE OF THE STUDY

The objective of the study was to further develop the already existing method of Roehl et al. (WO 2010/043512). The goal was the simultaneous detection of up to three miRNAs, such as, for example, miR16, miR210 and miR320, by means of differently charged PNAs in the context of using only one fluorescent dye. In the beginning, the detection of duplexes formed between miR16 and the differently modified PNAs was carried out from buffer which is free of biological matrix. In this respect, a neutral, a negatively charged PNA and a positively charged gamma-modified PNA were used.

Further, an HPLC method was to be established, which allows for the parallel detection of all three duplexes with a significant shift in retention time in only one HPLC run. Subsequently, the detection of miRNAs from biological matrixes such as human plasma, using this newly established method, was envisaged, as well as extending the detection to miR210 and miR320.

3. MATERIALS AND METHODS

3.1 Measurement of Optical Density

The extinction coefficients of miR16, miR210 and miR320 were determined by means of the Nearest-Neighbor Method (Tataurov et al. (2008) Biophysical Chemistry, 133:60-70), and the respective concentrations were calculated according to formula 1.

Calculation of the Concentration of $miR16$, $miR210$ and $miR320$ in $\mu M$ via the Optical Density ($OD$) with an Extinction Coefficient $\varepsilon_0$     Formula 1

$$\text{Concentration } [\mu M] = \frac{OD}{\varepsilon_0 \left[\frac{L}{mol \times cm}\right]} \times 1000000$$

In this respect, miRNA solutions of original concentration were diluted with Milli-Q Water to a final concentration of approximately 3 µm, respectively. The OD was measured three times with an Eppendorf BioPhotometer plus. For this, 200 µl of the 3 µM solution was used. An average value was calculated from three independent measurements and the concentration was determined using formula 1. The concentration of the stock solution can then be determined via the dilution factor.

3.2 Sample Preparation for HPLC Measurement

The sample preparation based on the hybridization of the miRNAs with complementary PNAs. For analysing miR16, first a hybridization buffer was made which was free of biological matrix. Subsequently, the hybridization was performed with human plasma, and hybridization was then also carried out with two further miRNAs, miR210 and miR320.

3.2.1 Materials and Reagents

The materials and reagents used for sample preparation are listed in Tables 1 and 2.

TABLE 1

Materials Used for Hybridization

| | Manufacturer |
|---|---|
| Mastercycler Gradient | Eppendorf AG |
| Thermomixer comfort 1.5 ml | Eppendorf AG |
| miniSpin plus | Eppendorf AG |
| Twin tec PCR Plate 96 | Eppendorf AG |
| LoBind Tube 0.5 ml | Eppendorf AG |
| LoBind Tube 1.5 ml | Eppendorf AG |

TABLE 2

Reagents Used for Hybridization

| | Manufacturer |
|---|---|
| Proteinase K, 50 µg/ml | Epicentre |
| 3M potassium chloride solution | Sigma-Aldrich |
| TRIZMA ® hydrochloride buffer solution; pH 8; 1M | Sigma-Aldrich |
| Urea 99.5% | Roth |
| Tween 20 | Sigma-Aldrich |
| Milli-Q-Water | Membra Pure Anlage |
| Tissue and Cell Lysis Solution | Epicentre |

3.2.2 Preparation of 0.1 µM miRNA Solutions and 1 µM PNA Solutions

From the miRNA stock solutions with a concentration as calculated according to formula 1, first a 1 µM solution was prepared which was subsequently diluted by a factor of 1:10. A solution with 10 vol.-% acetonitrile (ACN) and 0.01 vol.-% Tween 20 was used as diluent. Subsequently, from each of the lyophilized PNAs (see Table 3) obtained from Panagene (South Korea), 25 µM stock solutions were prepared by adding a solution with 10 vol.-% ACN and 0.01 vol.-% Tween 20. The stock solution were diluted with the same diluent by a factor of 1:25 for the hybridization.

TABLE 3

Modified PNA Strands with Respective Sequences. C = cysteine, O = O linker, E = glutamic acid, K = lysine, Atto425 = fluorescent dye, t = thymine, a = adenine, g = guanine, c = cytosine, * = lysine-gamma-modification

| PNA | Sequence |
|---|---|
| Neutral (SEQ ID NO: 1) | (Atto425)-C-OO-gcc aat att tac gtg ctg c-O-C(Atto425) |
| Negative (SEQ ID NO: 2) | (Atto425)-C-EEE-gcc aat att tac gtg ctg c-EEE-C(Atto425) |
| Pos. Gamma (SEQ ID NO: 3) | (Atto425)-C-OO-gcc* aat* att* tac* gtg* ctg c-O-C(Atto425) |

3.2.3 Lysate Preparation without Biological Matrix

Initially, a hybridization setup was chosen which was free of biological matrix. The composition of the hybridization buffer relies on an SDS-precipitated proteinase K-lysis buffer for cells and tissue. For 10 ml of lysis buffer, one needs 33 µl of proteinase K and 9967 µl of Tissue and Cell Lysis Solution. The hybridization buffer was then heated for 30 minutes at 65° C. and 350 rpm using a thermo-mixer. Subsequently, the solution was chilled on ice. As the SDS as part of the hybridization mixture would irreversibly damage the anion exchange column, it was precipitated with 1000 µl of 3M KCl solution, and the precipitate was then centrifuged for 15 minutes at 5° C. and 4000 rpm. For further use in the hybridization, the supernatant was separated on ice, and the SDS pellet was discarded.

3.2.4 Lysate Preparation with Biological Matrix Such as Human Plasma

Subsequently, the method was extended to the detection of miRNAs from human plasma. Human plasma, anticoagulated by the use of Na-heparin, was purchased from the company Dunn Labortechnik GmbH. Before a biological matrix can be used in the assay, all present nucleases (such as RNase A) need to be digested by a treatment with Proteinase K in Tissue and Cell Lysis Solution. For this, 3 ml plasma was digested with 7 ml lysis buffer, consisting of 2.9 ml Cell and Tissue Lysis Solution with 33 µl Proteinase K and 4.1 ml water, for 30 minutes at 65° C. Subsequently, the SDS was precipitated as described in item 3.2.3, centrifuged, and the pellet was discarded.

3.2.5 Hybridization

The hybridization mixture was set up according to the scheme provided in Table 4.

TABLE 4

| Hybridization Setup for 200 µl | | | | | | | |
|---|---|---|---|---|---|---|---|
| 100% ACN [µl] | H$_2$O [µl] | 1 µM PNA [µl] | 0.1 µM miR [µl] | 200 mM Tris pH 8 [µl] | Lysate without biol. matrix/human plasma [µl] | 8M urea [µl] | Total volume [µl] |
| 20 | 23.5 | 4 | 10 | 10 | 20 | 112.5 | 200 |

Hybridization was carried out under varying conditions. After a short heatup of the hybridization mixture to 95° C. for 5 minutes, the duplex between the PNA and miR16 was formed on ice. Hybridization at 25° C. was performed without any heating or cooling steps at room temperature. At first, the hybridization was carried out in the absence of urea. In addition, the effect of urea on the hybridization step was tested. Here, urea was used in the hybridization mixture at a concentration of 2 M and 4.5 M.

3.2.6 Generation of Calibration Samples for Single Measurements and Detection in Parallel For the calibration line, 0.1 µm of miR16 solution (see 3.2.2) was used. This solution was diluted by a factor of 1:5 in six subsequent dilution steps. A solution with 10 vol.-% of ACN and 0.01 vol.-% Tween 20 was used as diluent. The step of hybridizing was carried out in analogy to item 3.2.5. Here, the differently modified PNAs (see Table 3) were mixed with human plasma in hybridization buffer. The single dilution steps resulted in a row of concentration from 0.16 to 500 fmol miRNA per 100 µl injection. Since this method should allow for a parallel detection in one HPLC experimental setup, the hybridized solutions were mixed at a ratio of 1:1:1.

3.2.7 Sample Preparation for Single Measurements and Detection in Parallel of Duplexes Such as miR16-Neutral, miR210-Neutral and miR320-Neutral The hybridization of the miRNAs with the respective complementary PNAs was carried out as described in paragraph 3.2.5. First, complementary PNAs without modification and without any charges were chosen. For this, the 1 µM PNA solutions and the 0.1 µM miRNA solutions as described in 3.2.2 were used. For detection in parallel, all three samples were mixed at a ratio of 1:1:1 after hybridization.

3.2.8 Sample Preparation for Single Measurements and Detection in Parallel of Duplexes Such as miR320-Neutral, miR16-4-x-Negative and miR210-8-x-Negative To obtain a better chromatographic separation, PNAs were used for the next step of hybridization that had been modified by negative charges. Here, the PNA complementary to miR16 contained four negative changes, while the PNA complementary to miR210 contained eight negative charges. Both PNAs were synthesized by the company Panagene, South Korea (see Table 5).

TABLE 5

Modified PNA Strands with Corresponding Sequences. C = cysteine, O = O linker, E = glutamic acid, K = lysine, Atto425 = fluorescent dye, t = thymine, a = adenine, g = guanine, c = cytosine

| PNA | Sequence |
|---|---|
| miR320-neutral (SEQ ID NO: 4) | (Atto425)-OO-tcg ccc tct caa ccc ag-O-K(Atto425) |
| miR16-4-x negative (SEQ ID NO: 5) | (Atto425)-O-EE-gcc aat att tac gtg ctg c-EE-K(Atto425) |
| miR210-8-x negative (SEQ ID NO: 6) | (Atto425)-O-EEEE-cag tgt gcg gtg ggc ag-EEEE-K(Atto425) |

For hybridization, the 1 µM PNA solutions and the 0.1 µM miRNA solutions were used as described in paragraph 3.2.2. The hybridization was carried out for each of the miRNAs as described in 3.2.5. For the parallel detection, all three hybridization mixtures were mixed at a ratio of 1:1:1.

3.3 Establishing the HPLC Method
3.3.1 Buffer Preparation

The materials and reagents used for preparing the buffers are shown in Tables 6 and 7.

TABLE 6

Materials Used for Buffer Preparation

| | Manufacturer |
|---|---|
| Magnetic stirrer | RCT basic IKA Werke |
| pH-Meter 766 Calimatic | Knick |
| Measuring cylinder | Band Elerna Duran Silber |
| Filter Upper Cup 0.2 µm PES membrane, sterile | VWR |

TABLE 7

Reagents Used for Buffer Preparation

| | Manufacturer |
|---|---|
| Sodium Chlorid-Solution, 5M | AppliChem |
| LiChrosolv ® Acetonitril | Merck KGaA |
| Milli-Q-Wasser | Membra Pure Anlage |
| Natriumperchlorat-Monohydrat, ACS (≥98.0%) | Sigma-Aldrich |
| TRIZMA ® hydrochloride buffer solution; pH 7; 1M | Sigma-Aldrich |
| TRIZMA ® hydrochloride buffer solution; pH 8; 1M | Sigma-Aldrich |
| Natriumpyrophosphat-Decahydrat, ACS (≥98.0%) | Sigma-Aldrich |

Preparation of 5 M Sodium Perchlorate Stock Solution:

For 5 M $NaClO_4$ (sodium perchlorate) solution, a total of 702.30 g $NaClO_4 \times H_2O$ with a molar mass of 1240.46 g/mol were weighed and solved in 1 liter of water. The solution was subsequently filtered through a filter having a pore size of 0.2 µm.

Preparation of 0.1 M Sodium Pyrophosphate Stock Solution:

For the 0.1 M $Na_4P_2O_7$ (sodiumpyrophosphate) solution, a total of 22.3 g $Na_4P_2O_7 \times 10H_2O$ with a molar mass of 446.06 g/mol were weighed and solved in 500 ml $H_2O$.

HPLC Buffer 1 (pH 7)
Buffer A: 30 vol.-% ACN, 100 mM NaCl, 10 mM Tris-HCl pH7
Buffer B: 30 vol.-% ACN, 900 mM NaCl, 10 mM Tris-HCl pH7
Buffer C: 10 vol.-% ACN, 4 M $NaClO_4$ HPLC Buffer 2 (pH 8)
Buffer A: 30 vol.-% ACN, 100 mM NaCl, 10 mM Tris-HCl pH8
Buffer B: 30 vol.-% ACN, 900 mM NaCl, 10 mM Tris-HCl pH8
Buffer C: 10 vol.-% ACN, 4 M $NaClO_4$ 3.3.2 HPLC System
HPLC System 1

For HPLC analysis in the context of establishing the method, an HPLC Dionex Ultimate 3000 was used, encompassing a degaser, auto sampler, column oven and pump system. The detection was carried out using an RF fluorescence detector obtained from Dionex with an excitation wavelength of 436 nm and an emission wavelength of 484 nm and with a default detection sensitivity of Middle 4x.

HPLC System 2

For further analysis, an HPLC system Dionex Ultimate 3000 was used with a more sensitive fluorescence detector RF-20 A xs purchased from the company Shimadzu, with an excitation wavelength of 436 nm and an emission wavelength of 484 nm and with a default sensitivity of Middle 16x.

3.3.3 Summary of the Tested Parameters in the Context of HPLC Method Establishment.

For establishing the method, a DNAPAC®-100 Column with a length of 250 mm and a diameter of 4 mm was used. The column temperature varied between 30° C. and 60° C. In addition, the buffer system (see 3.3.1) and the gradient were adjusted. The injection volume was 100 µl, and the measurement was carried out at a flow rate of 1 ml/min.

3.4 Determination of the Melting Temperature $T_m$ of miRNAs

The melting temperature $T_m$ is defined as the temperature at the inflection point of the melting curve, at which the substance is present as 50% single-stranded. The analysis of the melting temperature with respect to miRNAs was carried out by measuring the UV absorption at 260 nm using a Beckman Counter DU800 UV/Vis spectrophotometer. A 1 µM solution in phosphate-buffered salt solution (PBS) was prepared for each miRNA. The samples were transferred to 350 µl microcuvettes and equilibrated for three minutes at 20° C. in the cuvette holder before heating to 80° C. at 0.5° C./min. At a temperature of 80° C., the samples were equilibrated for five minutes and subsequently chilled to 20° C. at 0.5° C./min. The UV absorption was measured in the temperature range from 20° C. to 80° C. at intervals of 1° C. The melting temperature was determined on the basis of the maximum of the first derivation, and this is the temperature at which 50% of the molecules are single-stranded and 50% are structured.

3.5 Detection of miR16, miR210 and miR320 from Human Plasma

All in all, ten plasma samples were analysed, which were provided by the group of Prof. Thum at the Hanover Medical School. Five of these plasma samples were derived from subjects of a control group, and another five plasma samples were derived from subjects diagnosed with an acute kidney injury. The plasma was treated with lysis buffer as described in chapter 3.2.4, and SDS was precipitated in the presence of potassium chloride solution. Subsequently, the samples were hybridized at 80° C., as outlined in the scheme of Table 8.

TABLE 8

Hybridization Mixtures for the Detection of mirR16, miR210 and miR320 Derived from Human Plasma.

| 100% ACN [µl] | PNA 1:1:1 mixture [µl] | 200 mM Tris pH 8 [µl] | Plasma [µl] | 8M urea [µl] | Total volume [µl] |
|---|---|---|---|---|---|
| 20 | 3 | 10 | 70 | 97 | 200 |

The PNAs of Table 5 were used for hybridization. For HPLC measurements, HPLC system 2 equipped with a detector sensitivity of Middle 16× was chosen (see 3.3.2), and the gradient was adjusted to 20-60% in buffer B within 7 minutes.

4. RESULTS

4.1 Concentrations of miRNAs

The extinction coefficients of miR16, miR210 and miR320, determined according to the Nearest-Neighbor method, are summarized in Table 9.

TABLE 9

Characteristics of the target molecules miR16, miR210 and miR230.
U = uracil, A = adenine, G = guanine, C = cytosine, p = 5'phosphate

| miRNA | Extinction Coefficient $\epsilon_0$[L/(mol*cm)] | Sequence |
|---|---|---|
| miR16 (SEQ ID NO: 7) | 226100 | 5'-pUAGCAGCACGUAAAUAUUGGCG-3' |
| miR210 (SEQ ID NO: 8) | 191700 | 5'-pAGCCCCUGCCCACCGCACACUG-3' |
| miR320 (SEQ ID NO: 9) | 232700 | 5'-pAAAAGCUGGGUUGAGAGGGCGA-3' |

To determine the exact concentration of the miRNAs, their respective optical densities were measured as described in chapter 3.1. The measurement resulted in a total of three single values, from which an average value was calculated. Based on the average value of the optical density and the respective theoretical extinction coefficients, concentrations were calculated according to formula 1 (see 3.1).

4.2 Optimization of Conditions for Hybridization

4.2.1 Influence of PNA Charges on Chromatographic Separation

When neutral PNAs are used for the detection of miRNA strands of similar length, no high quality chromatographic separation of the duplexes can be achieved. To evaluate the influence of additional positive and negative charges on the PNAs for the separation via HPLC, the following PNAs were used for the detection of miR16: neutral, negative and positive gamma (see Table 3).

These PNAs were all separately hybridized with miR16, as described under 3.2.5. This step of hybridizing comprises a short heating of the solution to 95° C. for 5 minutes, before the duplex between the PNA and miR16 is formed on ice. Subsequently, the samples were injected into the HPLC, and the chromatography was carried out at established conditions (see 4.3.4) at a gradient of 5-55% in buffer B within 9 minutes.

As shown in FIG. 2, the use of different surface charges of the PNA allowed a chromatographic separation of these three duplexes between miR16 and the respective complementary PNA. Further, additional peaks were observed in the area of the main peak, evoked by the hydrolysis of the maleimide ring present in the coupled Atto-fluorescent dyes, which resulted in additional negative charges in the duplex, which in turn also influenced the retention time.

The formation of half-peaks resulted in a reduction of chromatographic analysis and in a loss in sensitivity. Since the peak heights are decreased while the total peak area is similar, the signal-to-noise ratio is smaller.

The hydrolysis of the maleimide ring structure could be due to a hybridization temperature that is too high, or it could be the result of the composition of the hybridization buffer. To further evaluate these effects, the composition of the hybridization buffer and the influence of urea as part of the hybridization buffer were analysed. Since miRNAs have lower melting temperature in the presence of urea, the step of hybridization may also be carried out at lower temperatures.

4.2.2 Influence of the Hybridization Conditions on the HPLC Chromatograms

To evaluate the effect of the hybridization conditions on the chromatograms, miR16 was hybridized with differently charged PNAs on ice after the mixture was heated to 95° C. and 25° C., respectively. The conditions for hybridization are described in 3.2.5 and the conditions for chromatography are described in 4.3.4.

Decreasing the hybridization temperature resulted in a significantly lower amount of hydrolysis products. Thus, the splitting of peaks was significantly minimized, which in turn resulted in an increased signal intensity and, therefore, in an improved signal-to-sound ratio (see FIG. 3).

In Table 10, the effects of the lower hybridization temperatures are once more summarized. By reducing the hybridization temperature, hydrolysis of the maleimide ring, and thus the generation of shoulder peaks within the chromatogram, were avoided to the greatest possible extent. This effect is confirmed by the smaller retention times, which are higher due to additional negative charges, when the maleimide ring is hydrolysed at 95° C. In case of the main peak areas, the shoulder peak was not integrated when compared to the total peak area, which is constituted of the main peak area and the area of the shoulder peak.

TABLE 10

Influence of the Hybridization Conditions on the HPLC Chromatograms of miR16-neutral, miR16-negative and miR16-Pos. Gamma. $w_{0.5}$ = Peak Width at Half Height

| Duplex | Retention Time [min] | Main Peak Area [mV*min] | Total Peak Area [mV*min] | Relative Peak Area [%] | $w_{0.5}$ [min] | Peak Height [mV] |
|---|---|---|---|---|---|---|
| Hybridization 95° C., 25 min | | | | | | |
| miR16-Neutral | 8.33 | 4.4361 | 9.3205 | 47.60 | —* | 23.5796 |
| miR16-Negative | 9.50 | 6.0590 | 14.1564 | 42.80 | 0.1238 | 45.5080 |
| miR16-Pos. Gamma | 7.52 | 5.0343 | 10.4466 | 48.19 | 0.1622 | 30.8446 |
| Hybridization 25° C., 5 min | | | | | | |
| miR16-Neutral | 8.07 | 13.3816 | 15.3831 | 86.99 | 0.1053 | 103.9200 |
| miR16-Negative | 9.47 | 11.7880 | 15.0773 | 78.18 | 0.1132 | 94.7047 |
| miR16-Pos. Gamma | 7.25 | 12.3428 | 14.6106 | 84.48 | 0.1027 | 97.8214 |

*not analysable

While approximately a dublication of the main peak area was observed for miR16-negative at the lower hybridization temperature, a 2.5-fold increase was observed for miR16-Pos.Gamma, and even a 3-fold increase of the main peak area was observed in case of miR16-neutral. Besides a significant increase of the main peak area, an additional increase of peak height was also observed. From the data of Table 10, it can be seen that in case of the duplex between miR16 and the negative PNA, the peak height was even doubled. For miR16-neutral, a 4-fold increase, and for miR16-Pos. Gamma a 3-fold increase of peak height was reached as compared to an hybridization using a heating step of 95° C.

4.2.3 Hybridization in the Presence of Urea

In the case of longer incubation times of the samples within the auto sampler, the hydrolysis of the maleimide ring structure was observed to be increased. Therefore, the addition of urea at concentrations of 2 M and 4.5 M during the step of hybridization was tested. By way of comparison, a further hybridization in the absence of urea, according to chapter 3.2.5, was therefore carried out. The hybridization mixtures were subsequently measured by HPLC System 1 (see 3.3.2) under established HPLC conditions (see 4.3.4) after 0 h, 5.5 h and 11 h. To avoid any hydrolysis of the samples during these measurements, the auto sampler was cooled down to 4° C.

In case of the miR16-PNA samples without urea, one could observe a significant increase of the hydrolysis of the maleimide ring structure with increasing incubation times. As can be taken from FIG. 4, two shoulder peaks could be observed which were visible before and after the main peak in form of hydrolysis products. The shoulder peak which lies before the main peak may result from the separation of the phosphate at the 5'-end of miR16. The other peak is the opened maleimide ring. With increasing incubation time, each of these shoulder peaks increases which in turn results in a decrease of the main peak area.

As can be taken from FIG. 5, both of these side reactions could be avoided to large extends in the presence of urea. A direct comparison of the hybridization in the absence of urea and in the presence of 4.5 M urea showed a significant increase of the signal intensity in the presence of urea.

From the values shown in Table 11 it becomes clear to which extent the hydrolysis reaction can be avoided by the addition of urea. In case of miR16-neutral, the addition of 4.5 M urea to the hybridization mixture results in an increase of the main peak area by a factor of 1.1, while in case of the other duplexes miR16 negative and miR16-pos. gamma, the increase is by a factor of 1.2. In all three cases, an increase of the values by a factor of 1.2 could be observed with respect to peak heights. Hence, by using urea, the hydrolysis could be significantly reduced.

TABLE 11

Results from Hybridization without Urea in Comparison to Hybridization in the Presence of 4.5M Urea $w_{0.5}$ = Peak Width at Half Height

| Duplex | Retention Time [min] | Main Peak Area [mV*min] | Total Peak Area [mV*min] | Relative Peak Area [%] | $w_{0.5}$ [min] | Height [mV] |
|---|---|---|---|---|---|---|
| Hybridization without urea | | | | | | |
| miR16-Neutral | 5.38 | 14.9111 | 15.9557 | 93.45 | 0.1222 | 97.4115 |
| miR16-Negativ | 6.43 | 14.9110 | 16.3874 | 90.99 | 0.1298 | 93.4842 |
| miR16-Pos. Gamma | 4.69 | 12.9740 | 16.7800 | 77.32 | 0.1180 | 97.9023 |
| Hybridization in presence of 4.5M urea | | | | | | |
| miR16-Neutral | 5.40 | 16.3928 | 16.9169 | 96.90 | 0.1195 | 112.2993 |
| miR16-Negativ | 6.43 | 18.2576 | 18.3925 | 99.27 | 0.1263 | 113.3383 |
| miR16-Pos. Gamma | 4.69 | 15.5935 | 18.0915 | 86.19 | 0.1177 | 115.1840 |

4.2.4 Summary of the Optimized Hybridization Parameters

The hybridization experiments revealed that, in case of the duplexes between miR16 and the differently charged PNAs, the hydrolysis of the maleimide rings could not completely be inhibited by lowering the hybridization temperature to 25° C. and by adding 4.5 M of urea, but could be reduced to large amounts.

4.3 Optimization of the HPLC Method

4.3.1 Optimization of the Column Temperature

To evaluate the influence of the column temperature on the chromatographic resolution, different temperatures were tested. For this, samples were hybridized as described in paragraph 3.2.5. The hybridization took place at 40° C. Subsequently, the samples were measured according to the HPLC parameters as described in paragraph 4.3.4 at a temperature of 30° C., 40° C., 50° C., 55° C. and 60° C.

FIG. 6 shows the dependency of the peak area and the peak heights from the column temperature by way of example using miR16-negative. The increase of the column temperature resulted in a partial hydrolysis of the maleimide ring and thereby to the formation of additional negative charges on the PNA. These effects could be observed at temperatures of above 50° C. The increase of the column temperature from 30° C. to 50° C., however, resulted in a continuous increase of the main peak area and of the peak height. In the context of this experiment, a direct proportionality of the retention times from the column temperature could be observed. Accordingly, an increase of the column temperature results in higher retention times.

The data shown in Table 12 reveal the effect of the increase of the retention times due to an increased column temperature. An increase of the column temperature from 30° C. to 60° C. resulted in an increase of the retention time from 8.89 to 9.75 minutes. The optimal column temperature was shown to be 50° C., since at this temperature, the largest main peak area of 13.6 mV*min and the largest peak height of 104.9 mV could be achieved.

TABLE 12

Influence of the Column Temperature on the Retention Time of miR16-Negative. $w_{0.5}$ = Peak Width at Half Height.

| Duplex | Retention Time [min] | Main Peak Area [mV*min] | Total Peak Area [mV*min] | Relative Peak Area [%] | $w_{0.5}$ [min] | Height [mV] |
|---|---|---|---|---|---|---|
| miR16-Negativ | | | | | | |
| | column temperature 30° C. | | | | | |
| | 8.89 | 12.7723 | 19.9405 | 64.05 | 0.1297 | 89.3107 |
| | column temperature 40° C. | | | | | |
| | 9.18 | 12.4783 | 18.2977 | 68.20 | 0.1248 | 90.2145 |
| | column temperature 50° C. | | | | | |
| | 9.46 | 13.5899 | 17.0069 | 79.91 | 0.1153 | 104.8613 |
| | column temperature 55° C. | | | | | |
| | 9.61 | 10.5933 | 14.5225 | 72.94 | 0.1155 | 83.1685 |
| | column temperature 60° C. | | | | | |
| | 9.75 | 8.2809 | 11.2102 | 73.87 | 0.1098 | 68.9267 |

4.3.2 Optimization of the pH-Value

Since the pH influences the level of ionization of the PNA samples, and thereby their retention times, the optimization of the pH value was the next step to aim for the most optimal separation of these three duplexes. For this, HPLC column buffers with a pH of 7 and pH of 8 were tested. The respective buffer with a pH of 7 and a pH of 8 were generated as described in paragraph 3.3.1. Subsequently, the samples were hybridized according to 3.2.5 and were measured at these pH values under optimized HPLC conditions (see 4.3.4). These experiments showed that the increase of the pH value from 7 to 8 resulted in increased retention times. By increasing the pH value, an all over improved splitting of the peaks by avoiding hydrolysis of the maleimide ring and thereby a better signal intensity could be achieved. Increasing the pH value from 7 to 8 also improved the signal intensity. The signal intensity increased from 87.3 to 103.9 mV in case of miR16-neutral, from 86.3 to 94.7 mV in case of miR16-negative, and from 76.3 to 97.8 mV in case of miR16-pos. gamma. At the same time, one could observe an increase of the main peak area (see Table 13). In case of miR16-neutral, the main peak area increased from 12.8 to 13.4 mV*min. In case of miR16-negative, the main peak area increased from 9.9 to 11.8, and in case of miR16-pos. gamma, the main peak area increased from 11.6 to 12.3 mV*min.

TABLE 13

Influence of the pH Value on the Retention Times of miR16-Neutral, miR16-Negative and miR16-Pos. Gamma. $w_{0.5}$ = Peak Width at Half Height

| Duplex | Retention Time [min] | Mein Peak Area [mV*min] | Total Peak Area [mV*min] | Relative Peak Area [%] | $w_{0.5}$ [min] | Height [mV] |
|---|---|---|---|---|---|---|
| pH 7 | | | | | | |
| miR16-Neutral | 7.97 | 12.8299 | 15.5190 | 82.67 | 0.1255 | 87.2848 |
| miR16-Negativ | 9.31 | 9.9024 | 16.8621 | 58.73 | — | 86.3418 |
| miR16-Pos. Gamma | 7.12 | 11.5928 | 14.7677 | 78.50 | 0.1258 | 76.3084 |
| pH 8 | | | | | | |
| miR16-Neutral | 8.07 | 13.3816 | 15.3831 | 86.99 | 0.1053 | 103.9200 |
| miR16-Negativ | 9.47 | 11.7880 | 15.0773 | 78.18 | 0.1132 | 94.7047 |
| miR16-Pos. Gamma | 7.25 | 12.3428 | 14.6106 | 84.48 | 0.1027 | 97.8214 |

4.3.3 Optimization of the Gradients

After optimizing the pH value, it was the aim to adjust the gradient accordingly. In general, a flat gradient results in a better resolution. Higher signal intensities, however, are achieved with more steep gradients. The results of the gradient optimization are shown in Table 14. Initially, the gradient was carried out with an incline from 5-55% in buffer B in 9 minutes. This resulted in retention times of the three duplexes in the range between 7.25 and 9.47 minutes. Afterwards, the incline of the gradient was increased from 5.6 to 7.3% per minute. By increasing the initial salt concentration of buffer B from 5 to 15%, the total time of the run could be minimized from 17 to 15 minutes. The respective retention times were in the range of 4.84 to 6.47 minutes.

TABLE 14

Influence of Different Gradients on the Retention Times of miR16-Neutral, miR16-Negative and miR16-Pos. Gamma

| Duplex | Retention Time [min] |
|---|---|
| 5-55% Buffer B in 9 min (≙5.6%/min) | |
| miR16-Neutral | 8.07 |
| miR16-Negative | 9.47 |
| miR16-Pos. Gamma | 7.25 |
| 10-70% Buffer B in 9 min (≙6.7%/min) | |
| miR16-Neutral | 6.21 |
| miR16-Negative | 7.35 |
| miR16-Pos. Gamma | 5.45 |
| 15-80% Buffer B in 9 min (≙7.2%/min) | |
| miR16-Neutral | 5.42 |
| miR16-Negative | 4.85 |
| miR16-Pos. Gamma | 6.47 |
| 15-66% Buffer B in 7 min (≙7.3%/min) | |
| miR16-Neutral | 5.40 |
| miR16-Negative | 4.84 |
| miR16-Pos. Gamma | 6.47 |

4.3.4 Summary of Optimized HPLC Conditions

FIG. 7 shows the chromatogram of the separation of three duplexes between miR16-RNA and the respective three differently charged PNAs. In the void volume, the signal of the increased PNA excess is shown which is necessary to ensure that the duplex is completely formed. These three duplexes elude in the range of between 4 and 7.5 minutes. The HPLC running buffer had a pH of 8, the gradient had an incline of 15-66% in buffer B in 7 minutes. This incline of the gradient also revealed the required resolution.

4.4 Calibration of the HPLC Method

After optimizing the hybridization and the HPLC conditions, calibration of the established method was carried out. For this, a serial dilution was made which allowed for a calibration in the range of 0.16 and 500 fmol of the miRNA on the column (see 3.2.5). Subsequently, the samples were hybridized at 25° C. Since the aim was to allow for a parallel detection, an equimolar mixture of the respective serial dilution steps which were generated after the hybridization step was measured under established HPLC conditions (see 4.3.4). FIG. 8 shows the chromatograms which were obtained by the measurement of the respective serial dilutions. This figure shows the chromatograms of a 1:1:1 mixture of the respective serial dilution concentrations in which 0.053 to 166.7 fmol where injected. In case of injecting 0.267 fmol of miR16, the signal-noise-ratio (S/N) for miR16-pos. gamma is 2.2. In case of similar concentrations of miR16-Neutral and miR16-Negative, the signal-noise-ratio is 9.4 and 11.5, respectively. Consequently, in case of miR16-pos. gamma, the limit of detection (LOD) is approx. 0.267 fmol, wherein the same identical amount for both of the other duplexes could already be defined as the limit of detection (LOD). The lowest amount for calibration of 0.053 fmol could not be analyzed since this amount was underneath the limit of detection.

The respective calibration lines are shown in FIG. 9. In case of miR16-pos. gamma (FIG. 9 A), the incline is 0.1015 [(mV*min)/fmol] and the factor of correlations of $R^2$ is 0.9993. Here, a high accuracy was achieved, since the correlation factor is almost identical with the ideal value of 1.

The calibration line of miR16-neutral is shown in FIG. 9B. Here, the incline is 0.1254 [(mV*min)/fmol] and the correlation factor $R^2$ is 0.9966. The deviation from the last calibration point of miR16-neutral can clearly be seen, as already shown in FIG. 8. The correlation factor is 0.9966 and, therefore, lower in comparison to miR16-pos. gamma.

FIG. 9C shows the calibration line of miR16-negative. Here, the incline is 0.0889 [(mV*min)/fmol]. With $R^2=0.9999$, an already ideal correlation factor was achieved in this case.

4.5 Parallel Detection of miR16-Neutral, miR210-Neutral and miR320-Neutral

Since coupling of the fluorescence dye via maleimide chemistry goes along with a hydrolysis which is difficult to control, and a complete repression of hydrolysis failed to be achieved, another PNA design was chosen in the following by which the fluorescence dye was coupled in a more stable way to the PNAs via NHS chemistry.

In the next step, miR16, miR210 and miR320 should be detected in one HPLC column run. For this, the samples were first hybridized with their complementary neutral PNAs at 25° C. according to chapter 3.2.7, and a 1:1:1 mixture of these three miRNAs was subsequently generated. These samples were then measured using the HPLC system 2 (see 3.3.2) under established HPLC conditions (see. 4.3.4).

FIG. 10 shows the chromatograms of these three single measurements in comparison. Here, only a poor resolution of miR16-neutral and miR210-neutral is observed. Both duplexes reveal similar retention times.

Also with a 1:1:1 mixture, no satisfying resolution of these three duplexes, encompassing the neutral PNA and the respective miRNA, could be achieved. The chromatogram of the mixture of duplexes is in accordance with the peaks observed in the chromatogram of each of the separate duplexes.

4.6 Parallel Detection of miR320-Neutral, miR16-4× Negative and miR210-8× Negative For obtaining the optimal separation of the three duplexes, newly modified PNAs had to be used. Hereto, new PNAs were analyzed which are complementary to miR16 and miR210. To obtain an increased shift in retention time, the PNA complementary to miR16 was modified by the addition of two glutamic acid residues at each end of the sequence respectively, which resulted in four additional negative charges. The PNA complementary to miR210 was modified in a similar manner, but with eight negative charges. The PNA for miR320 was kept neutral.

The samples were subsequently hybridized at 25° C. as described in chapter 3.2.8, and then a 1:1:1 mixture of these hybridization mixtures was generated. Afterwards, the samples were measured using HPLC system 2 (see 3.3.2) under established HPLC conditions (see 4.3.4).

As can be taken from FIG. 11, an improved resolution profile could be achieved using this new PNA design. That is, a significantly improved separation as compared to FIG. 10 could be observed. Due to the negative charges of the respective PNAs, the respective retention times could be increased, as it was aimed for.

As evident from FIG. 12, these measurements are highly reproducible. The separation of the duplexes could also be achieved in a 1:1:1 mixture. It is also obvious from FIG. 12 that the peak area of miR16-4-x negative is significantly reduced in comparison to both other duplexes.

4.8 Detection of miR16, miR210 and miR320 Derived from Human Plasma

Subsequently, the detection of miR16, miR210 and miR320 from human plasma, provided by the Hannover Medical School, was carried out. Here, the correlation between acute kidney injury and the miRNAs as putative biomarkers was aimed to be analyzed.

Accordingly, five plasma samples from subjects of a control group (CTL) and five plasma samples from subjects with acute kidney injury (AKI), as described in paragraph 3.2.4, were digested and subsequently hybridized as described in chapter 3.5. Hybridization took place at 80° C. to destroy all putative secondary structures within miR320. The samples were subsequently measured using HPLC system 2 (see 3.3.2) using established HPLC conditions (see 4.3.4) with a gradient of 20-60% in buffer B for 7 minutes.

FIG. 13 shows the chromatograms obtained from the plasma sample of the subject out the control group (CTL 8) in comparison to the plasma of subject (AKI 154) with acute kidney injury. Here, one can clearly see that the emission of miR320 in case of AKI 154 is significantly higher than in case of the control subject CTL 8, while the emission of miR210 is almost similar in both cases.

Table 15 summarizes the values of miR16, miR210 and miR320 from human plasma. The respective ratios of miR210 and miR320 and the respective average values were calculated with standard deviations. The values of the plasma sample derived from subject AKI_138 were not considered as part of these calculations, since they are to considered as non-representative. The average value of the measurements with respect to the control subjects is in the range of 1.5 with a relative standard deviation of 17%. In case of patients with acute kidney injury, a higher average value of 2.6 was observed with lower relative standard deviation of 5%. In sum, all values are near the detection limit of the detector.

TABLE 15

Peak Areas for the Duplexes of miR16, miR210 and miR320 Derived from Human Plasma Provided by the Hannover Medical School with SD as Standard Deviation and RSD as Relative Standard Deviation

|  | Peak Area of miR210 [mV*min] | Peak Area of miR320 [mV*min] | Ratio 210/320 |
|---|---|---|---|
| Plasma_CTL_1 | 0.0053 | 0.0032 | 1.6 |
| Plasma_CTL_4 | 0.0016 | 0.0012 | 1.3 |
| Plasma_CTL_5 | 0.0064 | 0.0041 | 1.6 |
| Plasma_CTL_7 | 0.0050 | 0.0028 | 1.8 |
| Plasma_CTL_8 | 0.0046 | 0.0036 | 1.3 |
| Average Value | 0.0046 | 0.0030 | 1.5 |
| SD | 0.0020 | 0.0013 | 0.3 |
| RSD [%] | 44% | 43% | 17% |
| Plasma_AKI_124 | 0.0054 | 0.0020 | 2.7 |
| Plasma_AKI_136 | 0.0053 | 0.0022 | 2.4 |
| Plasma_AKI_138 | 0.0062 | 0.0236 | 0.3 |
| Plasma_AKI_152 | 0.0049 | 0.0020 | 2.5 |
| Plasma_AKI_154 | 0.0046 | 0.0017 | 2.7 |
| Average Value | 0.0053 | 0.0020 | 2.6 |
| SD | 0.0007 | 0.0002 | 0.1 |
| RSD [%] | 13% | 10% | 5% |

6. SUMMARY

The newly established HPLC method developed in this work allows for the simultaneous detection of different miRNAs with similar length in one HPLC run. In this context, three miRNAs, namely miR16, miR210 and miR320, were separated via AEX-HPLC after hybridization in the presence of differently charged PNAs. At first, a PNA design was chosen which allowed for a coupling of the fluorescence dye to the PNA sequence via maleimide chemistry. However, this turned out not to be optimal since the chromatograms, in the course of optimizing the hybridization and HPLC conditions, revealed a splitting of the peaks and, thereby, a minimized signal intensity due to the hydrolysis of the maleimide ring. This effect was in particular observed at increased temperatures and after longer incubation times of the samples.

It followed that a new PNA design was chosen which allowed for the coupling of the fluorescence dye via NHS ester chemistry. This resulted in a stability of the samples and the peak splitting was successfully avoided.

Using the new PNA design, it was possible to quantitatively detect two miRNAs (210 and 320) from human plasma. In sum, an increased ratio of miR210 vs. miR320 was observed in the plasma derived of the subjects with acute kidney injury in comparison to the control group.

According to person communications, this trend was independently confirmed by PCR analysis.

The detection method of the present invention thus allows for using the miRNAs miR210 and miR320 as a biomarker in the diagnosis of acute kidney injury. As a consequence, the HPLC method developed in the context of the present invention enables the development of a diagnostic kit which allows for a quick and simple method to diagnose this particular disease at an early stage, thereby ensuring an early treatment of patients.

The invention claimed is:

1. A method for quantitatively detecting at least three distinct oligonucleotides of equal length in parallel from one biological sample, said method comprising the steps of:
  a) providing a biological sample containing or suspected of containing the at least three distinct oligonucleotides of equal length;
  b) forming a hybridization mixture by contacting the biological sample with at least three detection molecules complementary to the at least three distinct oligonucleotides of equal length to form at least three hybridized detection molecule-oligonucleotide moieties, wherein the at least three detection molecules are each labelled with at least one fluorescent moiety, and wherein the at least three detection molecules have different surface charges;
  c) separating the at least three hybridized detection molecule-oligonucleotide moieties from non-hybridized detection molecules by anion exchange high performance liquid chromatography (AEX-HPLC); and
  d) detecting the at least three hybridized detection molecule-oligonucleotide moieties by means of quantitative fluorescence readout.

2. The method of claim 1, wherein the at least three distinct oligonucleotides have a length of from 10 to 50 nucleotides.

3. The method of claim 1, wherein at least three distinct oligonucleotides of equal length are selected from the group consisting of micro RNAs (miRNAs), small interfering RNAs (siRNAs), short activating RNAs (saRNAs), decoy oligonucleotides, antisense oligonucleotides, aptamers, and spiegelmers.

4. The method of claim 1, wherein the detection molecule is selected from the group consisting of peptide nucleic acids (PNAs), phosphorodiamidate morpholino oligomers (PMOs) and ugimers.

5. The method of claim 1, wherein the at least three detection molecules have a length of from 10 to 30 nucleotides.

6. The method of claim 1, wherein the at least three detection molecules are each labelled with a fluorescent moiety of the same identity.

7. The method of claim 1, wherein the different surface charges of the at least three detection molecules are selected from the group consisting of neutral, negative and positive charges any combination thereof.

8. The method of claim 7, wherein the negative surface charge(s) is/are characterized by the presence of at least two incorporated negatively charged amino acid residues or aminoglycine backbone modifications.

9. The method of claim 8, wherein the negatively charged amino acid residues are in the form of glutamic acids.

10. The method of claim 7, wherein the positive surface charge(s) is/are characterized by the presence of at least two incorporated positively charged amino acid residue or aminoglycine backbone modifications.

11. The method of claim 10, wherein the positively charged amino acid residues are in the form of lysine.

12. The method of claim 1, wherein the AEX-HPLC of step c) is performed at a temperature of from 30° C. to 75° C.

13. The method of claim 1, wherein the quantitative fluorescence readout of step d) is characterized by comparing the fluorescent signals of the at least three hybridized detection molecule-oligonucleotide moieties to an internal standard or to an external standard in form of an external calibration curve.

14. The method of claim 1, wherein the detection molecules have a length of from 10 to 20 nucleotides.

15. The method of claim 1, wherein the detection molecules have a length of from 15 to 20 nucleotides.

16. The method of claim 1, wherein the different surface charges of the at least three detection molecules are a combination of neutral and negative charges, neutral and positive charges, and/or negative and positive charges.

17. The method of claim 1, wherein the different surface charges of the at least three detection molecules are selected from multiple negative charges, multiple positive charges, and any combination thereof.

18. The method of claim 1, wherein the AEX-HPLC of step c) is performed at a temperature of from 40° C. to 55° C.

19. The method of claim 1, wherein the AEX-HPLC of step c) is performed at a temperature of 50° C.

* * * * *

UNITED STATES PATENT AND TRADEMARK OFFICE
CERTIFICATE OF CORRECTION

PATENT NO. : 10,400,269 B2
APPLICATION NO. : 15/554456
DATED : September 3, 2019
INVENTOR(S) : Ingo Rohl et al.

It is certified that error appears in the above-identified patent and that said Letters Patent is hereby corrected as shown below:

In the Claims

Claim 7, Column 44, Line 41:
Please insert the word --and-- between the words "charges" and "any"

Signed and Sealed this
Twenty-sixth Day of November, 2019

Andrei Iancu
*Director of the United States Patent and Trademark Office*